(12) United States Patent
Bina et al.

(10) Patent No.: US 8,846,330 B2
(45) Date of Patent: Sep. 30, 2014

(54) METHODS AND KITS FOR THE DIAGNOSIS OF RYR1-RELATED DISEASES

(75) Inventors: Saiid Bina, Gaithersburg, MD (US); Rolf Bunger, McLean, VA (US)

(73) Assignee: The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 177 days.

(21) Appl. No.: 13/062,654

(22) PCT Filed: Sep. 8, 2009

(86) PCT No.: PCT/US2009/056239
§ 371 (c)(1),
(2), (4) Date: May 18, 2011

(87) PCT Pub. No.: WO2010/028372
PCT Pub. Date: Mar. 11, 2010

(65) Prior Publication Data
US 2011/0212483 A1 Sep. 1, 2011

Related U.S. Application Data

(60) Provisional application No. 61/095,055, filed on Sep. 8, 2008.

(51) Int. Cl.
*C12Q 1/02* (2006.01)
*G01N 33/68* (2006.01)
*G01N 33/50* (2006.01)
*C12Q 1/00* (2006.01)
*C12Q 3/00* (2006.01)

(52) U.S. Cl.
CPC ........ *G01N 33/6872* (2013.01); *G01N 2800/40* (2013.01); *G01N 33/5091* (2013.01)
USPC ............................................... 435/29; 435/4

(58) Field of Classification Search
None
See application file for complete search history.

(56) References Cited

PUBLICATIONS

Rosenberg, Henry; et al; "Testing for Malignant Hyperthermia." Anesthesiology, 96, 232-237, 2002.*
McKinney, Leslie C.; et al; "Characterization of Ryanodine Receptor-mediated Calcium Release in Human B Cells." Anesthesiology, 104, 1191-1201, 2006.*
Litman, Ronald S.; et al; "Malignant Hyperthermia: Update on Suseptibilty Testing." Journal of the American Medical Association, 293, 2918-2924, 2005.*
Baur, C.P.; et al; "A Multicenter Study of 4-Chloro-m-cresol for Diagnosing Malignant Hyperthermia Susceptibility." Anesthesia & Analgesia, 90, 200-205, 2000.*
Lewis, Richard S; "Calcium Signaling Mechanisms in T Lymphocytes" Annual Review of Immunology, 19, 497-521, 2001.*
Fredholm, BB; "Adenosine, and endogenous distress signal, modulates tissue damage and repair" Cell Death and Differentiation, 14, 1315-1323, 2007.*
Sei, Patients with Malignant Hyperthermia Demonstrate an Altered Calcium Control Mechanism in B Lymphocytes, Anesthesiology, 97, 1052-1058, 2002.
Butanda-Ochoa, Modulation of the Skeletal Muscle Ca2+ Release Channel/Ryanodine Receptor by Adenosine and Its Metabolites : A Structure-Activity Approach, Bioorganic & Medicinal Chemistry, 11, 3029-3037, 2003.
Girard, B-Lymphocytes from Malignant Hyperthermia-Susceptible Patients have an Increased Sensitivity to Skeletal Muscle Ryanodine Receptor Actvators, The Journal of Biological Chemistry, 276, 48077-48082, 2001.
McKinney, Characterization of Ryanodine Receptor-Mediated Calcium Release in Human B Cells, Anesthesiology, 104, 1191-1201, 2006.
Laver, Regulation of the Calcium Release Channel from Rabbit Skeletal Muscle by the Nucleotides ATP, AMP, IMP and Adenosine, Journal of Physiology, 537.3, 763-778, 2001.
Bina, A Novel Minimally-Invasive In Vitro Diagnostic Test for Malignant Hyperthermia in Humans, Anesthesiology, 109, A879, 2008.

* cited by examiner

*Primary Examiner* — Blaine Lankford
*Assistant Examiner* — David Berke-Schlessel
(74) *Attorney, Agent, or Firm* — Morgan, Lewis & Bockius LLP

(57) ABSTRACT

The present invention encompasses methods for diagnosis of calcium channel related diseases (e.g., RyR1-related diseases) comprising contacting lymphocytes isolated from a subject with a calcium channel agonist (e.g., an RyR1 agonist), measuring the adenosine and inosine produced by the lymphocytes; and comparing the measured levels in the sample to the adenosine and inosine levels in a normal control, whereby an increase in the adenosine and inosine levels relative to the control is indicative of a calcium channel related disease (e.g., RyR1-related disease). The invention also encompasses kits for diagnosis of calcium channel-related diseases.

11 Claims, 14 Drawing Sheets

METHODS AND KITS FOR THE DIAGNOSIS OF RYR1-RELATED DISEASES

RELATED APPLICATIONS

The present application is a U.S. National Phase Application of International Application No. PCT/US2009/056239 (filed Sep. 8, 2009) which claims priority to U.S. Provisional Application No. 61/095,055 (filed Sep. 8, 2008) which are hereby incorporated by reference in their entirety.

GOVERNMENT SUPPORT

The present invention arose in part from research funded by grant numbers R080BS, R080DN and R080DS. The Government may have certain rights in the invention.

BACKGROUND OF THE INVENTION

In skeletal muscle, excitation-contraction coupling involves a physical interaction between two different types of $Ca^{2+}$ channels: the voltage-gated $Ca^{2+}$ channels dihydropyridine receptors (DHPRs) located in the sarcolemma and the intracellular $Ca^{2+}$ release channels of ryanodine receptor type 1 (RyR1) located on the sarcoplasmic reticulum (SR) membrane. In response to sarcolemmal depolarization, DHPRs undergo a conformational change that activates nearby RyR1. The subsequent massive release of SR $Ca^{2+}$ into the myoplasm activates the contractile machinery. The DHPR-RyR1 mechanical interaction is bidirectional since RyR1 proteins dramatically enhance the ability of the DHPR to function efficiently as a $Ca^{2+}$ conducting ion channel (Nakai et al., Nature 380:72-75 (1996); Dulhunty et al., Prog. Biophys. Mol. Biol. 79:45-75 (2000)).

Relaxation requires the ATP-dependent re-uptake of cytosolic $Ca^{2+}$ into the SR or the removal of $Ca^{2+}$ into the extracellular space by the sarcolemmal $Ca^{2+}$ pump. Since the $Ca^{2+}$ gradients across both cell and SR membranes are of the order of four magnitudes, cells expend a huge amount of energy to return elevated cytoplasmic $Ca^{2+}$ to basal physiologic levels, i.e., to maintain $Ca^{2+}$ control and homeostasis. This energetic effort can be revealed and quantitated by measuring the production of the ATP catabolites adenosine and inosine (Bünger, R. In: Topics and perspectives in adenosine research, pp. 223-235 (1987); Bünger, R. and S. Soboll, Eur J. Biochem 159: 203-13 (1986)), even when using a non-contractile cell model such as lymphocytes in an in vitro set-up.

Four clinically distinct hereditary human and muscle disorders are known to be associated with point mutations and deletions in the RyR1 gene: malignant hyperthermia (MH), central core disease (CCD), multiminicore disease (MmD), and nemaline rod myopathy (NM) (Jurkat-Rott, et al., J. Neural. 249:1493-1502 (2002); Taratuto A L. Curr Opin. Neural. 15:553-561 (2002)). In addition, heat, exercise, and stress induced muscle syndromes may be related to RyR1 defects, to some degree.

Malignant hyperthermia (MH) is a pharmacogenetic syndrome of skeletal muscle whose primary symptom is an abnormal response to volatile anesthetics and depolarizing skeletal muscle relaxants. Exposure to these agents during surgery can trigger uncontrolled $Ca^{2+}$ release from the SR mainly through a mutated RyR1 gene leading to abnormal sensitivity of the RyR1 receptor. The increased intracellular $Ca^{2+}$ load triggers a cascade of biochemical events that results in muscle rigidity, rhabdomyolysis, cardiac arrhythmia, acidosis, and eventually lethal hyperthermia. If not treated promptly by withdrawing the anesthetic and administration of dantrolene (an intracellular calcium blocker), the only drug available for MH episode treatment, mortality is extremely high (>80%). Initial MH symptoms can have a slow, clinically ambiguous onset, making an imminent MH episode difficult to recognize. Heat, stress, and exercise are other conditions that can induce MH-like symptoms.

Currently definitive MH diagnosis is made by means of the invasive, surgery-requiring caffeine halothane contracture test (CHCT) in North America, by a similar in vitro contracture test (IVCT) in Europe and by technically very difficult calcium induced calcium release (CICR) in Japan; all these tests use biopsied leg muscle (Vasitis lateralis). Other countries are using tests essentially similar to one or these tests. CHCT has a sensitivity of 97% (accurately detects MH susceptible individuals) with a specificity of only 78% (yields 22% false positives). However, because of the invasive surgery, the costs of the test, and the limited viability of the biopsied skeletal muscle samples, the CHCT must be completed within 5 hours post biopsy. Therefore, the muscle biopsies must be conducted at a certified MH diagnostic center or in close-by hospitals (currently there are only 6 MH diagnostic centers in North America). Because of these procedural and logistic complexities, it is estimated that only about 10% of all individuals eligible to undergo the CHCT test are actually tested (estimated from referrals to the North American Malignant Hyperthermia Hotline).

Central core disease (CCD) (also called Shy-Magee syndrome) is a hereditary myopathy characterized by proximal muscle weakness and skeletal deformities of the lower limbs (Taratuto A L. Curr Opin Neurol 15:553-561 (2002)). Diagnosis of CCD is established through histological identification of single, large amorphous areas of reduced oxidative enzyme activity in central or peripheral regions of Type I muscle fibers (i.e., central cores). However, in some CCD individuals, cores are not centrally located, but instead are found in peripheral regions of the muscle fiber. Furthermore, resting $Ca^{2+}$ levels are apparently not elevated by CCD mutations that result in excitation-contraction uncoupling, indicating that an elevation in resting $Ca^{2+}$ is not an absolute requirement for core formation (Avila et al., J. Gen. Physiol. 118: 277-290 (2001); Avila et al., J. Gen. Physical. 121:277-286 (2003)).

Specific variants of multiminicore disease (MmD) (Ferreira et al., Ann. Neurol. 51:750-759 (2002); Jungbluth et al., Eurology 59:284-287 (2002)) and nemaline rod myopathy (NM) (Scacheri et al., Neurology 55:1689-1696 (2000)) have recently been shown to be also associated with mutations in the RyR1 gene. Skeletal muscle biopsies of patients suffering from MmD display multifocal, poorly circumscribed and short core-like lesions, whereas skeletal muscle obtained from individuals with NM exhibit rod-like structures when visualized using Gomori's trichrome stain in both Type I and II skeletal muscle fibers.

Significant clinical overlap exists between these related muscle disorders. For example, early-stage CCD may first present as a minicore myopathy (Ferreiro et al., Ann. Neurol. 51:750-75 (2002)), nemaline rods have been found adjacent to central cores in biopsies of some CCD patients (Scacheri et al., Neurology 55:1689-1696 (2000)), and CCD patients are often found to be MH susceptible (MHS), but MHS patients are unlikely to be CCD.

What is needed is a less complex, less time consuming, less invasive and more economical method for testing for RyR1 related diseases.

SUMMARY OF THE INVENTION

One aspect of the present invention relates to methods for diagnosing calcium channel related diseases (such as e.g., RyR1-related diseases) in a subject. Accordingly, one embodiment of the invention is a method for detecting a calcium channel related disease in a subject comprising: (a) contacting lymphocytes isolated from the subject with calcium channel agonist; (b) measuring the adenosine and inosine produced by the lymphocytes; and (c) comparing the measured levels in the sample to the adenosine and inosine levels in a normal control, wherein an increase in the adenosine and inosine levels relative to the control is indicative of a calcium channel related disease.

In one embodiment, the calcium channel related disease is an RyR1-related disease and the calcium channel agonist is an RyR1 agonist. In another embodiment, the RyR1-related disease is malignant hyperthermia, central core disease, multiminicore disease or nemaline rod myopathy. In yet another embodiment, the RyR1 agonist is 4-chloro-m-cresol, ryanodine, halothane, thiopental, caffeine, or mixtures thereof. In an alternate embodiment, the RyR1 agonist is 4-chloro-m-cresol.

In one embodiment, lymphocytes are in a blood sample from the subject. In an alternate embodiment, the lymphocytes are peripheral blood lymphocytes.

In another embodiment, the normal control comprises levels of adenosine and inosine produced by lymphocytes from a subject not suffering from a calcium channel related disease. In yet another embodiment, the calcium channel related disease is an RyR1-related disease and the normal control comprises levels of adenosine and inosine produced by lymphocytes from a subject not suffering from an RyR1-related disease.

In the methods of the invention, an increase in the adenosine and inosine levels relative to the control is also indicative of a deletion or mutation in the RyR1 gene. Thus, in one embodiment: the deletion, or mutation in the RyR1 gene is indicative of a skeletal muscle-related disorder. Furthermore, in the methods of the invention, an increase in the adenosine and inosine levels relative to the control is also indicative of a deletion or mutation in a gene controlling the expression and/or function of a calcium channel.

In one embodiment, subject is a human. In another embodiment, the subject is a pig. In another embodiment, the method comprises from about 0.1 mM to about 10 mM of an RyR1 agonist.

In an alternate embodiment, the method of detecting an RyR1 related disease includes the steps of: isolating lymphocytes from a sample; treating the isolated lymphocytes with a RyR1 agonist; determining adenosine and inosine levels in the treated sample; and producing a diagnosis based on the adenosine and inosine levels in the treated sample. The RyR1-related disease may be one of malignant hyperthermia (MH), central core disease (CCD), multiminicore disease (MmD), and nemaline rod myopathy (NM). In one embodiment, the RyR1-related disease is MH. The isolated lymphocytes may be peripheral blood lymphocytes. In one embodiment, the RyR1 agonist is one of 4-chloro-m-cresol (4CmC), ryanodine, halothane, thiopental and caffeine. In an alternate embodiment, the RyR1 agonist is 4CmC. In one embodiment, the adenosine and/or inosine level in the treated sample is determined by HPLC.

In another embodiment, the subject is a human, pig, horse, dog or mouse.

Another aspect of the present invention relates to kits for diagnosis of calcium channel related diseases (such as e.g., RyR1-related diseases) in a mammal. One embodiment of the invention is a kit for detecting a calcium channel related disease in a subject comprising (1) a calcium channel agonist, (2) a normal control comprising a sample of solution containing levels of adenosine and inosine equivalent to levels produced by lymphocytes from a normal individual and (3) a positive control comprising levels of adenosine and inosine equivalent to levels produced by lymphocytes from a subject with a calcium channel related disease.

In one embodiment of the invention, the calcium channel related disease is an RyR1 related disease and the calcium channel agonist is an RyR1 agonist. In one embodiment, the kit is for detecting an RyR1-related disease and comprises (1) an RyR1 agonist, (2) a normal control comprising a sample of solution containing levels of adenosine and inosine equivalent to levels produced by lymphocytes from a normal individual and (3) a positive control comprising levels of adenosine and inosine equivalent to levels produced by lymphocytes from a subject with a an RyR1-related disease. In one embodiment, the RyR1 agonist is 4-chloro-m-cresol, ryanodine, halothane, thiopental, caffeine, or mixtures thereof which may be supplied in concentrations ranging from about 0.1 mM to about 10 mM of an RyR1 agonist. In one embodiment, the levels of adenosine and inosine in the positive control are 2- to 8-fold greater than the levels of adenosine and inosine in the normal control.

In one embodiment, the kit for detecting an RyR1 related disease includes a RyR1 agonist, $HClO_4$, and standards for adenosine and inosine. In another embodiment, the kit further includes a heprinized blood collection tube. In an alternate embodiment, the kit further includes a peripheral blood lymphocytes isolation agent. In yet another related embodiment, the kit further includes a label or a label with instructions.

BRIEF DESCRIPTION OF THE DRAWINGS

The foregoing summary, as well as the following detailed description of the invention, will be better understood when read in conjunction with the appended figures. For the purpose of illustrating the invention, shown in the figures are embodiments of the present invention. It should be understood, however, that the invention is not limited to the precise arrangements, examples, and instrumentalities shown.

* XeC (10 mM) Significantly (P=0.002) Reduced 4CmC (2 mM)-Induced Adenosine

Figure 14:
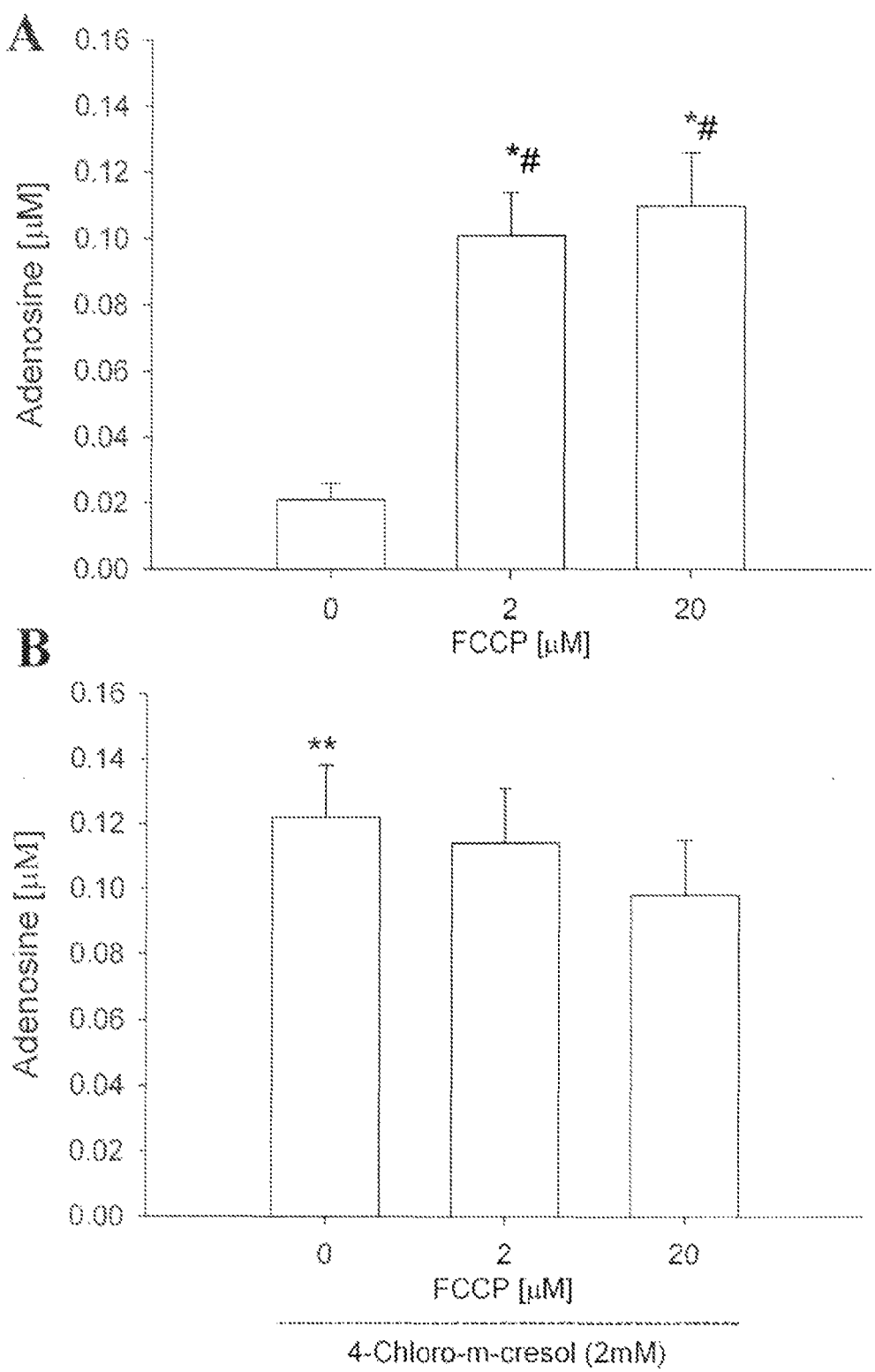

FIG. 14 shows the effect of Carbonyl cyanide 4-(trifluoromethoxy) phenylhydrazone (FCCP) on swine lymphocyte cells. FIG. 14A shows the effect of carbonyl cyanide 4-(trilluoromethoxy) phenylhydrazone (FCCP) alone on swine lymphocyte cells. FIG. 14B shows the effect of FCCP on 4-chloro-m-cresol (4CmC)-induced adenosine in swine lymphocyte cells. Briefly, (FIG. 14A) lymphocyte cells from normal swine (n=5) in suspension in $Ca^{2+}/Mg^{2+}$ free Hanks' balanced salt solution (HBSS) in the presence of adenosine deaminase inhibitor, with and without FCCP were incubated at 37° C. for 10 minutes. In another set of experiments (FIG. 14B), the same conditions that was used for experiments of FIG. 14A was used except at the end of a 10 minute-incubation period, samples were treated with 2 mM 4CmC and bathed for additional 30 to 45 minutes. At the end of the incubation period, samples reactions were terminated as detailed in the Example 4. The number of the cells used was normalized to represent per million cells. FIG. 14A: * FCCP (2 and 20 µM) significantly increased basal adenosine levels. # Values are not statistically different from corresponding values in FIG. 14B.  In the absent of MCPC, 4CmC-induced adenosine (FIG. 14B) was 5.8 fold higher compared with basal adenosine level in FIG. 14A**.

DETAILED DESCRIPTION

This invention relates to novel minimally invasive in vitro diagnostic tests for calcium channel related diseases (e.g., RyR1-related diseases (such as e.g., MH)) and kits suitable for carrying out these tests. Specifically, the invention relates to minimally-invasive tests and kits for carrying out these tests for diagnosis and post-treatment follow-up of calcium channel related diseases, such as e.g., RyR1-related syndromes, whose common denominator and etiology are related to intracellular $Ca^{2+}$ overload with obligatory consequences on the cell, energetically reflected in altered production of ATP catabolites such as adenosine and inosine.

Applicants have discovered that treatment of lymphocytes with a calcium channel agonist can be used as an indicator for a calcium channel related disease. Applicants have also discovered that treatment of lymphocytes with an RyR1 agonist can be used as an indicator for RyR1-related disease.

Without being bound by theory, Applicants postulate that adenosine (ADO) release from lymphocyte cells are a measure of RyR1 function, and that mutations in the RyR1 gene that lead to abnormal agonist-induced $Ca^{2+}$ release in skeletal muscle will also lead to irregular ADO release in lymphocyte cells. Furthermore, without being bound by theory, it is thought that the RyR1 gene can play a central role in all of these syndromes through the excess release of $Ca^{2+}$ from the sarcoplasmic reticulum (SR), resulting in cellular $Ca^{2+}$ overload, but via different molecular mechanisms.

The practice of the present invention employs, unless otherwise indicated, conventional methods of diagnosis, biochemistry, histology, cell biology, microbiology, immunology, and molecular biology within the skill of the art. Such techniques are explained fully in the literature.

As used herein, the term "subject" refers to any animal classified as a mammal, including, but not limited to, rats, mice, rabbits, guinea pigs, non-human primates, and humans, as well as domestic and farm animals such as cats, dogs, horses, cattle, cows, pigs, sheep, chickens and ducks.

As used herein, the term "calcium channel related disease" refers to any disease that is associated with a malfunction of a calcium channel. Exemplary calcium channel related diseases include but are not limited to diabetes, starvation, and RyR1-related diseases. Exemplary RyR1-related diseases include, but are not limited to, malignant hyperthermia (MH), central core disease (CCD), multiminicore disease (MmD), and nemaline rod myopathy (NM).

As used herein, the abbreviation "MH" refers to malignant hyperthermia. As used herein, the abbreviation, "CCD" refers to central core disease which is also known as Shy-Magee syndrome. Furthermore, as used herein, the abbreviation "MmD" refers to multiminicore disease and the abbreviation "NM" refers to nemaline rod myopathy. As used herein, the term "central core disease" also encompasses Shy-Magee syndrome.

Diagnostic Methods

One aspect of the invention is minimally invasive diagnostic methods for detecting calcium channel related diseases (such as e.g., RyR1-related symptoms (diseases)) in a subject. In general, the methods of the invention are based on measurements of ATP catabolite (e.g., adenosine and inosine) changes upon calcium channel agonist stimulation in lymphocytes isolated from a subject.

In one embodiment, the methods of the invention are based on measurements of ATP catabolite (e.g., adenosine and inosine) changes upon RyR1 agonist stimulation in lymphocytes isolated from a subject. Optimally, in one embodiment of the invention, the methods take advantage of the discoveries that RyR1 is present in lymphocytes and the differences in RyR1 gene expression in patients is compared to normal controls.

In general, the methods of the invention comprise contacting lymphocytes isolated from a subject (i.e., a patient in need thereof) with a calcium channel agonist, measuring the adenosine and inosine produced by lymphocytes and producing a diagnosis based on the adenosine and inosine levels compared to that of normal cells, whereby an increase is indicative of a calcium channel related disease.

One embodiment of the invention is a method for detecting a calcium channel related disease in a subject comprising (a) contacting lymphocytes isolated from the subject with a calcium channel agonist, (b) measuring the adenosine and inosine produced by the lymphocytes, and (c) comparing the measured levels in the sample to the adenosine and inosine levels in a normal control, whereby an increase in the adenosine and inosine levels relative to the control is indicative of a calcium channel related disease.

Another embodiment of the invention is a method for detecting a calcium channel related disease in a subject comprising (a) contacting lymphocytes isolated from the subject with a calcium channel agonist, (b) measuring the adenosine produced by the lymphocytes, and (c) comparing the measured levels in the sample to the adenosine levels in a normal control, whereby an increase in the adenosine levels relative to the control is indicative of a calcium channel related disease.

In one embodiment, the subject is a human, dog, cat, horse, pig or mouse. In another embodiment, the subject is a human.

In another embodiment, the lymphocytes are in a blood sample from the subject. In yet another embodiment, the lymphocytes are peripheral blood lymphocytes.

In an alternate embodiment, the step of contacting comprises incubating the lymphocyte sample with the agonist under suitable conditions. Suitable incubation conditions include, but are not limited to, 37° C. in the presence of a buffer. In one embodiment, the step of contacting comprises incubating the lymphocyte sample with the agonist at least overnight, preferably for at least one or two days.

In one embodiment of the invention, the calcium channel related disease is an RyR1-related disease and the calcium channel agonist is an RyR1 agonist. Thus, another embodiment of the invention is a method for diagnosing an RyR1-related disease in a subject comprising the steps of isolating lymphocytes from a sample taken from the subject, treating the isolated lymphocytes with a RyR1 agonist, determining adenosine and inosine levels of the treated lymphocytes; and producing a diagnosis based on the adenosine and inosine levels. In another embodiment, the calcium channel related disease is an RyR1-related disease and the method for detecting the disease in a subject comprises (a) contacting lymphocytes isolated from the subject with an RyR1 agonist, (b) measuring the adenosine and inosine produced by the lymphocytes, and (c) comparing the measured levels in the sample to the adenosine and inosine levels in a normal control, whereby an increase in the adenosine and inosine levels relative to the control is indicative of an RyR1-related disease.

RyR1-related diseases include, but are not limited to, malignant hyperthermia (MH), central core disease (CCD), multiminicore disease (MmD), and nemaline rod myopathy (NM). In one embodiment, the RyR1-related disease is MH. In another embodiment, the RyR1-related disease is CCD. In another embodiment, the RyR1-related disease is MmD. In another embodiment, the RyR1-related disease is NM.

Calcium channel agonists are well known to a person of ordinary skill in the art. Any known calcium channel agonist is suitable for use in the methods of this invention. Exemplary suitable calcium channel agonists include but are not limited to IP3 receptor agonists, agonists to mitochondrial calcium stores, 4-chloro-m-cresol (4CmC), ryanodine, caffeine, thiopental, succinylcholine, and volatile anesthetics such as halothane, isoflurane and enflurane.

RyR1 agonists are well known to a person of ordinary skill in the art. Any RyR1 agonist is suitable for use in the methods of this invention. Exemplary suitable RyR1 agonists include, but are not limited to, 4-chloro-m-cresol (4CmC), ryanodine, caffeine, thiopental, succinylcholine, and volatile anesthetics such as halothane, isoflurane and enflurane. In one embodiment, the RyR1 agonist is 4CmC. In another embodiment, the RyR1 agonist is 4-chloro-m-cresol (4CmC), ryanodine, halothane, thiopental, caffeine, or mixtures thereof.

In one embodiment, the concentration of the calcium channel agonist ranges from about 0.1 mM to about 10 mM, alternatively from about 1 mM to about 10 mM, alternatively from about 1 to about 5 mM, alternatively from about 0.2 mM to about 3, 4, 5, 6, 7, 8, 9, or 10 mM. In one embodiment, the calcium channel agonist is 4CMC which is used at a concentration ranging from about 0.1 mM to about 5 mM, alternatively from about 1 mM to about 5 mM. In another embodiment, the calcium channel agonist is caffeine which is used at a concentration ranging from about 0.1 mM to about 10 mM.

In one embodiment, the calcium channel related disease is an RyR1-related disease and the concentration of RyR1 agonist ranges from about 0.1 mM to about 10 mM, alternatively from about 1 mM to about 10 mM, alternatively from about 1 to about 5 mM, alternatively from about 0.2 mM to about 3, 4, 5, 6, 7, 8, 9, or 10 mM. In one embodiment, the RyR1 agonist is 4CMC which is used at a concentration ranging from about 0.1 mM to about 5 mM, alternatively from about 1 mM to about 5 mM, alternatively from about 0.5 mM to about 5 mM. In another embodiment, the RyR1 agonist is caffeine which is used at a concentration ranging from about 0.1 mM to about 10 mM, alternatively from about 10 mM to about 50 mM. In an alternate embodiment, the RyR1 agonist is ryanodine which is used at a concentration from about 0.5 µM to about 5 µM In one embodiment, the adenosine and inosine produced by the lymphocytes isolated from a subject suffering from a calcium channel related disease (such as e.g., an RyR1-related disease) are 2, 3, 4, 5, 6, 7 or 8 fold or more greater than the adenosine and inosine levels in the normal control. In one embodiment, the adenosine and inosine produced by the lymphocytes isolated from a subject suffering from a calcium channel related disease (such as e.g., an RyR1-related disease) are 2, 3, 4, 5, 6, 7 or 8 fold or more greater than the adenosine and inosine levels in lymphocytes from a subject not suffering from the calcium channel related disease (such as e.g., the RyR1-related disease).

The adenosine and inosine produced by the lymphocytes can be determined by any suitable method including but not limited to high-performance liquid chromatography (HPLC), luminescence method, liquid chromatography-mass spectrometry (LC-MS), and adenosine biosensor having entrapped enzymes adenosine deaminase, nucleoside phosphorylase, and xanthine oxidase. In one embodiment, the adenosine and inosine levels are determined using the luminescence method described by Jabs et. al. (*Clin. Chem.* 36/1, 81-87 (1990)), the disclosure of which is incorporated by reference in its entirety.

In one embodiment of the invention, the normal control comprises lymphocytes from a subject that is not suffering from a calcium channel related disease. In another embodiment, the normal control is a diagnostic control database developed for each calcium channel disease.

In one embodiment, the calcium channel related disease is an RyR1-related disease and the normal control comprises lymphocytes from a subject that is not suffering from an RyR1-related disease. In another embodiment, the calcium channel related disease is an RyR1-related disease and the normal control is a diagnostic control database developed for each RyR1-related disease.

Optionally the methods of the invention may further utilize an inhibitor of adenosine deaminase. Suitable inhibitors are commonly known in the art. Exemplary suitable inhibitors are EHNA, 2'-deoxycoformycin, FR 234938, and pentostatin. In one embodiment, the inhibitor of adenosine deaminase is added along with the calcium channel agonist (e.g., the RyR1 agonist).

An increase in the adenosine and inosine levels relative to the control is indicative of a deletion or mutation in a gene controlling the expression and/or function of a calcium channel. Accordingly, in one embodiment of the invention, the methods of the invention can be used to test for a deletion or mutation in a gene controlling the expression and/or function of a calcium channel.

In another embodiment, an increase in the adenosine and inosine levels relative to the control is also indicative of a deletion or mutation in the RyR1 gene, i.e., an RyR1 defect. Thus, the methods of the invention can be used to test for a deletion or mutation in the RyR1 gene. In one embodiment, the deletion or mutation in the RyR1 gene is indicative of a skeletal muscle-related disorder, such as e.g., rhabdomyolysis.

In one embodiment, the method of detecting/diagnosing a calcium channel related disease in a subject comprises the steps of (1) drawing a venous blood sample from a patient; (2) isolating lymphocytes from the whole blood sample; (3) treating cells with a known calcium channel agonist (e.g., 4CmC, caffeine or ryanodine); (4) purification of the sample; (5) analysis for total adenosine and inosine levels (via e.g., HPLC); and (6) comparing the results of the analysis to a standard control database or normal control (i.e., a sample from normal lymphocytes) whereby an increase in the total adenosine and inosine levels is indicative the calcium channel related disease. In another embodiment, the calcium channel related disease is an RyR1 related disease and the method of detecting/diagnosing the disease in a subject comprises the steps of: (1) drawing a venous blood sample from a patient; (2) isolating lymphocytes from the whole blood sample; (3) treating cells with a known RyR1 agonist (e.g., 4CmC, caffeine or ryanodine); (4) purification of the sample; (5) analysis for total adenosine and inosine levels (via e.g., HPLC); and (6) comparing the results of the analysis to a standard control database or normal control (i.e., a sample from normal lymphocytes) whereby an increase in the total adenosine and inosine levels is indicative the RyR1-related disease.

Figure 1:
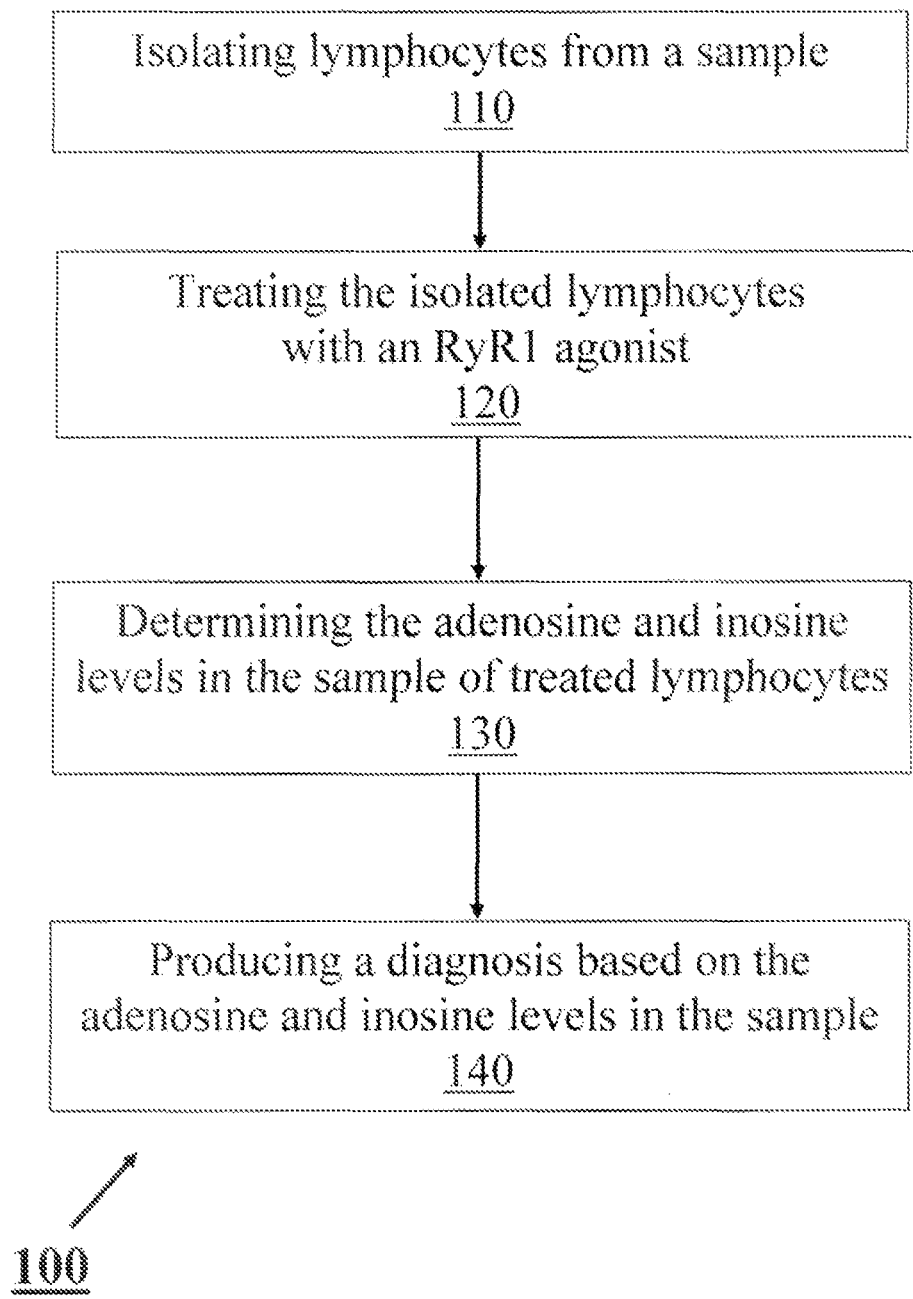
FIG. 1 is a flow chart showing an exemplary diagnosis method for RyR1-related diseases (an example of a calcium channel related disease).

Referring now to FIG. 1, one embodiment of the invention is method 100 for the diagnosis of RyR1-related diseases which comprises the steps of: isolating (110) lymphocytes from a subject; treating (120) the isolated lymphocytes with a RyR1 agonist; determining (130) adenosine and inosine levels in the sample of the treated lymphocytes; and producing (140) a diagnosis based on the adenosine and inosine levels in the sample. Those of skill in the art would understand that the method 100 can also be used for other calcium channel related diseases.

The lymphocytes can be isolated from the subject using methods well-known in the art. In one embodiment, the lymphocytes are peripheral blood lymphocytes isolated from a blood sample of the subject. Preferably, the blood sample is stored in a heparinized tube and the peripheral blood lymphocytes are collected using the Ficoll-Hypaque centrifugation technique.

In one embodiment, diluted anti-coagulated blood is layered over Ficoll-Hypaque and centrifuged. Red blood cells and polymorphonuclear leukocytes or granulocytes are denser and centrifuge through the Ficoll-Hypaque, while mononuclear cells consisting of lymphocytes together with some monocytes band over it and are recovered at the interface followed by washing the cells with a buffer such as e.g., Hanks' balanced salt solution (HBSS), and re-suspending cells in the buffer at a concentration of approximately 50 to $250 \times 10^3$ cells/test tube.

The cells are diluted to a desired concentration and are treated (step 120) with different concentrations of specific RyR1 agonist in the presence of absence of an inhibitor of adenosine deaminase. In one embodiment, the cells are treated with different concentrations of the RyR1 agonist 4CmC (0 to 10 mM) at 37° C. in the presence and absence of inhibitor of adenosine deaminase erythro-9-(2-hydroxy-3-nonyl) adenine (EHNA, 0.1 mM) for about 30 minutes.

The adenosine and inosine levels in the sample can be determined (step 130) using a variety of methods, including, but not limited to, high-performance liquid chromatography (HPLC), luminescence method, adenosine biosensor consisting of three entrapped enzymes adenosine deaminase, nucleoside phosphorylase, and xanthine oxidase, and by using LC-MS instead of the HPLC system.

In one embodiment, RyR1 agonist-treated cell suspension (e.g., after a 30 minute incubation with the RyR1 agonist) is mixed with an equal volume of 6% $HClO_4$ and centrifuged at 6000 rpm for 10 minutes. Aliquots of supernatant are analyzed with HPLC for the adenosine and inosine levels.

In another embodiment, re-suspended cells are counted using a hemocytometer. In an alternate embodiment, the adenosine and inosine levels are determined using a reverse phase microbore column HPLC and UV detector.

In yet another embodiment, the adenosine and inosine levels are determined using a microbore column HPLC with a photodiode array detector (PAD). The microdialysis samples are injected directly onto a microbore C18 reverse-phase column without any prior sample preparation. Use of a PAD in this method provides many advantages. First, a PAD allows the simultaneous detection of UV absorbance at multiple wavelengths, allowing the detection of each compound at its maximal UV absorbance. Further, the full UV absorption spectrum is recorded for each detected peak, confirming peak purity and identity. Using a microbore HPLC column and detection of UV absorbance at the maximal absorbance for each compound improves the sensitivity for all compounds.

The diagnosis (step 140) is accomplished by comparison of the adenosine and inosine levels in the sample to the adenosine and inosine levels in a normal control. In one embodiment, the normal control comprises lymphocytes from a subject that does not suffer from an RyR1-related disease. In another embodiment, diagnosis (step 140) is accomplished by comparison of the HPLC analysis results of the subject to a normal control such as e.g., diagnostic control database derived from normal B lymphocytes (i.e., lymphocytes isolated from normal volunteer subjects). A significant increase of adenosine and inosine levels after RyR1 agonist stimulation indicates high likelihood RyR1-related diseases such as e.g., MH.

Kits

Another aspect of the invention relates to kits for the diagnosis of calcium channel related diseases (such as e.g., RyR1-related diseases) i.e., kits for carrying out the methods of the invention. In one embodiment, the kit for detecting a calcium channel related disease in a subject comprises (1) a calcium channel agonist, (2) a normal control comprising a sample of solution containing levels of adenosine and inosine equivalent to levels produced by lymphocytes from a normal individual and (3) a positive control comprising levels of adenosine and inosine equivalent to levels produced by lymphocytes from a subject with a calcium channel related disease.

In another embodiment, the kit for detecting a calcium channel related disease in a subject comprises (1) a calcium channel agonist, (2) a normal control comprising a sample of solution containing levels of adenosine equivalent to levels produced by lymphocytes from a normal individual and (3) a positive control comprising levels of adenosine equivalent to levels produced by lymphocytes from a subject with a calcium channel related disease.

In another embodiment, the kit further includes a heparinized blood collection tube and a peripheral blood lymphocytes isolation agent. In an alternate embodiment, the kit further includes a label. In another related embodiment, the kit further includes a label with instruction; preferably, a procedure instruction.

In an alternate embodiment, the calcium channel related disease is an RyR1 related disease and the calcium channel agonist is an RyR1 agonist. In one embodiment, the calcium channel related disease is an RyR1 related disease and the kit comprises (1) an RyR1 agonist, (2) a normal control comprising a sample of solution containing levels of adenosine and inosine equivalent to levels produced by lymphocytes from a normal individual and (3) a positive control comprising levels of adenosine and inosine equivalent to levels produced by lymphocytes from a subject with an RyR1 related disease. In another embodiment, the calcium channel related disease is an RyR1 related disease and the kit comprises at least an RyR1 agonist, $HClO_4$ and standards for adenosine and inosine (i.e., a normal control).

In a related embodiment, the RyR1 related disease is selected from a group consisting of malignant hyperthermia (MH), central core disease (CCD), multiminicore disease (MmD), and nemaline rod myopathy (NM). In another embodiment, the RyR1-related disease is MH. In alternate embodiment, the RyR1 related disease is CCD. In another related embodiment, the RyR1 agonist is one of 4-chloro-m-cresol (4CmC), ryanodine, halothane, thiopental, caffeine, or mixtures thereof. In another related embodiment, the RyR1 agonist is 4CmC. In another related embodiment, the RyR1 agonist is caffeine. In yet another related embodiment, the RyR1 agonist is 4CmC.

In one embodiment of the invention, the kit comprises from about 0.1 mM to about 10 mM of a calcium channel agonist such as e.g., an RyR1 agonist. In another embodiment of the invention, the levels of levels of adenosine and inosine in the positive control are 2 to 8 fold greater than the levels of adenosine and inosine in the normal control.

The invention also provides for kits for detecting a deletion or mutation in a gene controlling the expression and/or function of a calcium channel and for kits for detecting a deletion and/or mutation in the RyR1 gene.

One embodiment of the invention is a kit for detecting a deletion and/or mutation in a gene controlling the expression and/or function of a calcium channel in a subject comprising (1) a calcium channel agonist, (2) a normal control comprising a sample of solution containing levels of adenosine and inosine equivalent to levels produced by lymphocytes from a normal individual and (3) a positive control comprising levels of adenosine and inosine equivalent to levels produced by lymphocytes from a subject having deletion and/or mutation in a gene controlling the expression and/or function of a calcium channel.

Another embodiment of the invention is a kit for detecting a deletion and/or mutation in the RyR1 gene in a subject comprising (1) an RyR1 agonist, (2) a normal control comprising a sample of solution containing levels of adenosine and inosine equivalent to levels produced by lymphocytes from a normal individual and (3) a positive control comprising levels of adenosine and inosine equivalent to levels produced by lymphocytes from a subject having deletion and/or mutation in the RyR1 gene.

Without further description, it is believed that one of ordinary skill in the art can, using, the preceding description and the following illustrative examples, make and utilize the present invention and practice the claimed methods. The following examples therefore, specifically point out the preferred embodiments of the present invention, and are not to be construed as limiting in any way the remainder of the disclosure.

EXAMPLES

Example 1

In Vitro Studies for Detecting Malignant Hyperthermia Susceptibility in Humans Pilot studies were conducted using blood samples from human subjects in the following groups: Group 1: MHS subjects with positive CHCT and/or having a known MH associated mutation (n=11); Group 2: non-MH susceptible with negative CHCT results (MHN) (n=9), and Group 3: normal subjects who had not undergone CHCT and had no family history of MH (n=7).

The experimental results are listed in Tables 1 and 2. Table 1 shows the biometric data, proband status, and adenosine plus inosine levels for pre and post 4-chloro-m-cresol (4CmC) treatment of lymphocyte cells obtained from three subject groups.

TABLE 1

Biometric data, proband status, and adenosine levels for pre and post 4-chloro-m-cresol (4CmC, 5 mM) treatment of lymphocyte cells obtained from three subject groups.

| Subject number | CHCT Diagnosis | Sex | CHCT Results Contractures* (g) 3% Hal | 2 mM Caf | Know MH mutation | Basal [Adenosine] ($\mu$M) | [Adenosine] $\mu$M Post 5 mM 4CmC | Medical or family history |
|---|---|---|---|---|---|---|---|---|
| 111606 | Positive | M | 4.5 | 0.7 | Yes | 0.17 | 2.079 | Rhabdo |
| 031606 | Positive | M | 1.9 | 0.3 | Yes | 0.137 | 1.932 | H |
| 112106 | Positive | M | 1.2 | 0 | Yes | 0.271 | 1.580 | H |
| 082207 | Positive | M | 1.4 | 0.3 | In process | 0.425 | 1.725 | H |
| 102207 | Positive | F | 2.1 | 0.4 | Yes | 0.262 | 0.949 | H |
| 031808 | Positive | F | 1.3 | 0 | In process | 0.264 | 1.475 | H |
| 102507 | Positive | M | 0.8 | 0.2 | Yes | 0.302 | 0.987 | Rhabdo |
| 061708 | Positive | M | 0.8 | 0 | Yes | 0.177 | 0.853 | Rhabdo |
| 061808B | N/P | F | N/P | N/P | Yes | 0.103 | 0.984 | H |
| 061808D | N/P | M | N/P | N/P | Yes | 0.226 | 1.240 | H |
| 061808E | Positive | F | — | — | Yes | 0.146 | 1.560 | H |
| 061808C | Negative | M | N/P | N/P | NO | 0.056 | 0.128 | H |
| 042407 | Negative | M | 0 | 0 | N/P | 0.022 | 0.078 | H |
| 092507 | Negative | M | 0 | 0 | N/P | 0.012 | 0.070 | Rhabdo |
| 020508 | Negative | M | 0.4 | 0 | N/P | 0.040 | 0.074 | Rhabdo |
| 120407 | Negative | M | 0 | 0 | N/P | 0.043 | 0.249 | H |
| 042208 | Negative | M | 0.4 | 0 | N/P | 0.006 | 0.192 | Rhabdo |
| 042908 | Negative | F | 0.3 | 0 | N/P | 0 | 0.140 | Rhabdo |
| 061008 | Negative | M | 0.5 | 0 | N/P | 0.093 | 0.237 | Rhabdo |
| 071508 | Negative | M | 0.2 | 0 | N/P | 0.170 | 0.356 | H |
| 081407 | Normal | M | N/P | N/P | N/P | 0.096 | 0.220 | None |
| 091307 | Normal | F | N/P | N/P | N/P | 0.078 | 0.144 | None |
| 013008 | Normal | M | N/P | N/P | N/P | 0.062 | 0.246 | None |
| 013108 | Normal | M | N/P | N/P | N/P | 0.014 | 0.154 | None |
| 013108K | Normal | M | N/P | N/P | N/P | 0.036 | 0.276 | None |
| 051308RK | Normal | M | N/P | N/P | N/P | 0.07 | 0.177 | None |
| 051308C | Normal | M | N/P | N/P | N/P | 0.092 | 0.268 | None |

In Table 1, Rhabdo means a patient with rhabdomyolysis episode; H means a patient with alleged MH episode or having a family history of MH; CHCT means caffeine halothane contracture test; N/P is not performed; M is male; F is female; Caf means caffeine; Hal means halothane.

Table 2 shows the biometric data, proband status, and adenosine plus inosine levels for pre and post 4-chloro-m-cresol (4CmC) treatment of lymphocyte cells obtained from three subject groups.

TABLE 2

Biometric data, proband status, and adenosine plus inosine levels for pre and post 4CmC treatment of lymphocyte cells obtained from three subject groups

| Subject Number | Diagnosis | CHCT Results Contractures* (g) 3% Hal | 2 mM Caf | Know MH mutation | Basal Adenosine + Inosine (μM) | Adenosine + Inosine Post 5 mM 4CmC | Medical or family history | Sex |
|---|---|---|---|---|---|---|---|---|
| 111606 | MHS | 4.5 | 0.7 | Yes | 5.8 | 55.6 | Rhabdo | M |
| 031606 | MHS | 1.9 | 0.3 | Yes | 4.8 | 52.3 | H | M |
| 112106 | MHS | 1.2 | 0 | Yes | 6.2 | 42.5 | H | M |
| 082207 | MHS | 1.4 | 0.3 | In process | 4.1 | 23.9 | H | M |
| 102207 | MHS | 2.1 | 0.4 | Yes | 6.2 | 29.2 | H | F |
| 031808 | MHS | 1.3 | 0 | In process | 9.2 | 42.3 | H | F |
| 102507 | MHS | 0.9 | 0.2 | Yes | 6.1 | 24.9 | Rhabdo | M |
| 061708 | MHS | 0.8 | 0 | Yes | 7.1 | 23.5 | Rhabdo | M |
| 061808B | MHS | N/P | N/P | Yes | 3.2 | 26.7 | H | F |
| 061808D | MHS | N/P | N/P | Yes | 8.3 | 28.5 | H | M |
| 061808E | MHS | N/P | N/P | Yes | 4.8 | 42 | H | F |
| 061808C | MHN | N/P | N/P | No | 1.1 | 6.5 | H | M |
| 042407 | MHN | 0 | 0 | N/P | 0.9 | 2.4 | H | M |
| 092507 | MHN | 0 | 0 | N/P | 0.3 | 2 | Rhabdo | M |
| 020508 | MHN | 0.4 | 0 | N/P | 1.4 | 6.3 | Rhabdo | M |
| 120407 | MHN | 0 | 0 | N/P | 0.5 | 6 | H | M |
| 042208 | MHN | 0.4 | 0 | N/P | 0.7 | 5 | Rhabdo | M |
| 042908 | MHN | 0.3 | 0 | N/P | 2.9 | 3.9 | Rhabdo | F |
| 061008 | MHN | 0.5 | 0 | N/P | 3.5 | 6.7 | Rhabdo | M |
| 071508 | MHN | 0.2 | 0 | N/P | 5.2 | 9.6 | H | M |
| 081407 | Normal | N/P | N/P | N/P | 2.7 | 4.4 | None | M |
| 091307 | Normal | N/P | N/P | N/P | 0.6 | 1.5 | None | F |
| 013008 | Normal | N/P | N/P | N/P | 2.4 | 6.7 | None | M |
| 013108 | Normal | N/P | N/P | N/P | 3.2 | 5.5 | None | M |
| 013108K | Normal | N/P | N/P | N/P | 1.5 | 5.1 | None | M |
| 051308K | Normal | N/P | N/P | N/P | 2.9 | 5.8 | None | M |
| 051308C | Normal | N/P | N/P | N/P | 4.9 | 8.6 | None | M |

*3% halothane and 2 mM caffeine induced contractures are average of contractures from 3 muscle strips.

In Table 2, MHS means malignant hyperthermia susceptible; MHN means malignant hyperthermia non-susceptible; Rhabdo means a patient with rhabdomyolysis episode; H means a patient with alleged MH episode or having a family history of MH; CHCT means caffeine halothane contracture test; N/P is not performed; M is male; F is female; Caf means caffeine; Hal means halothane.

Briefly, venous blood samples (20 ml) were drawn from patients using heparinized blood collection tubes. Peripheral blood lymphocyte cells were isolated from whole blood by the Ficoll-Hypaque centrifugation technique. Briefly, diluted anti-coagulated blood is layered over Ficoll-Hypaque and centrifuged. Mononuclear cells consisting of lymphocytes and some monocytes are recovered at the interface. The cells were washed with the Flanks' balanced salt solution (HBSS) buffer, re-suspended in the HBSS buffer, and treated with different concentration of 4CmC at 37° C. in the presence and/or absence of inhibitor of adenosine deaminase erythro-9-(2-hydroxy-3-nonyl)adenine (EHNA) for about 30 minutes. The cells were then purified by adding an equal volume of 6% $HClO_4$ and centrifuged at 6000 rpm for 10 minutes. Aliquots of the supernatant were analyzed for adenosine and inosine content with HPLC using a Waters Separation Module (Model 2695) equipped with Waters Photodiode Array Detector and Empower software.

Figure 2:
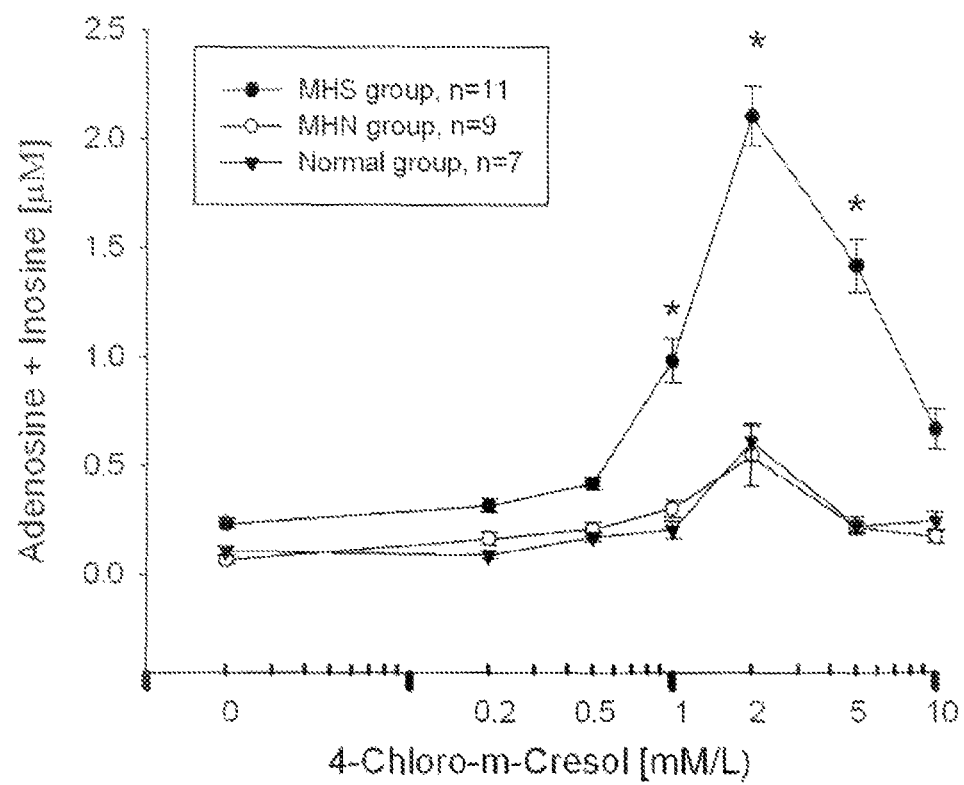
FIG. 2 is a dose-response curve for 4-chloro-m-cresol (4CmC)-induced intracellular adenosine plus inosine in lymphocyte cells from malignant hyperthermia susceptible (MHS, n=11), not-susceptible (MHN, n=9), and normal (n=7) subjects. Lymphocyte cells were treated with 4CmC in the presence of an inhibitor of adenosine deaminase (EHNA, 0.1 mM). After purification, aliquot was analyzed for adenosine and inosine content using HPLC. Adenosine plus inosine values in the absence of 4CmC are plotted against X=0.02 mM to allow logarithmic display of the entire dose response curve. Adenosine plus inosine levels were normalized to reflect per 1 million cells. 4CmC responses at 1, 2, and 5 mM on MHS groups are about 4, 4, and 6 fold higher than the corresponding values in MI-1N or normal groups with values of $6 \times 10^{-5}$, $8 \times 10^{-5}$, and $5.5 \times 10^{-7}$, respectively. There were no overlaps between the MHS group and the MHN or normal groups.
Figure 3:
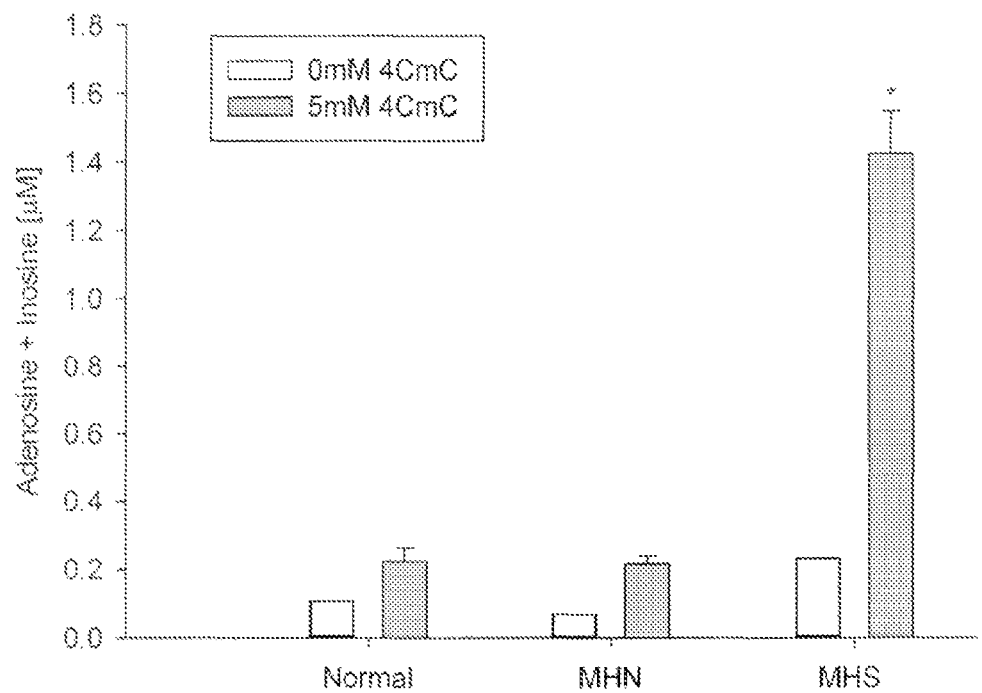
FIG. 3 shows the effect of 4-chloro-m-cresol (4CmC) on adenosine and inosine levels in lymphocyte cells from subjects susceptible to malignant hyperthermia (MHS), non-susceptible to MH (MHN), and from normal subjects. Lymphocyte cells from MHS (n=11), MHN (n=9) and normal (n=7) subjects were suspended in normal HBSS plus 0.1% BSA and treated with adenosine deaminase inhibitor (EHNA, 0.1 mM). After 10 minutes of incubation at 37° C., cells were treated with HBSS, with and without the RyR1 agonist 4CmC (5 mM) and incubated at 37° C. for an additional 45 minutes. After termination and purification of the samples, aliquots (50 µl) were assayed in duplicate for adenosine and inosine content using HPLC. Concentrations are normalized to per 1 million cells. The sum of the adenosine plus inosine level is about 6-fold higher than corresponding values in normal and MHN cells.
Figure 5:
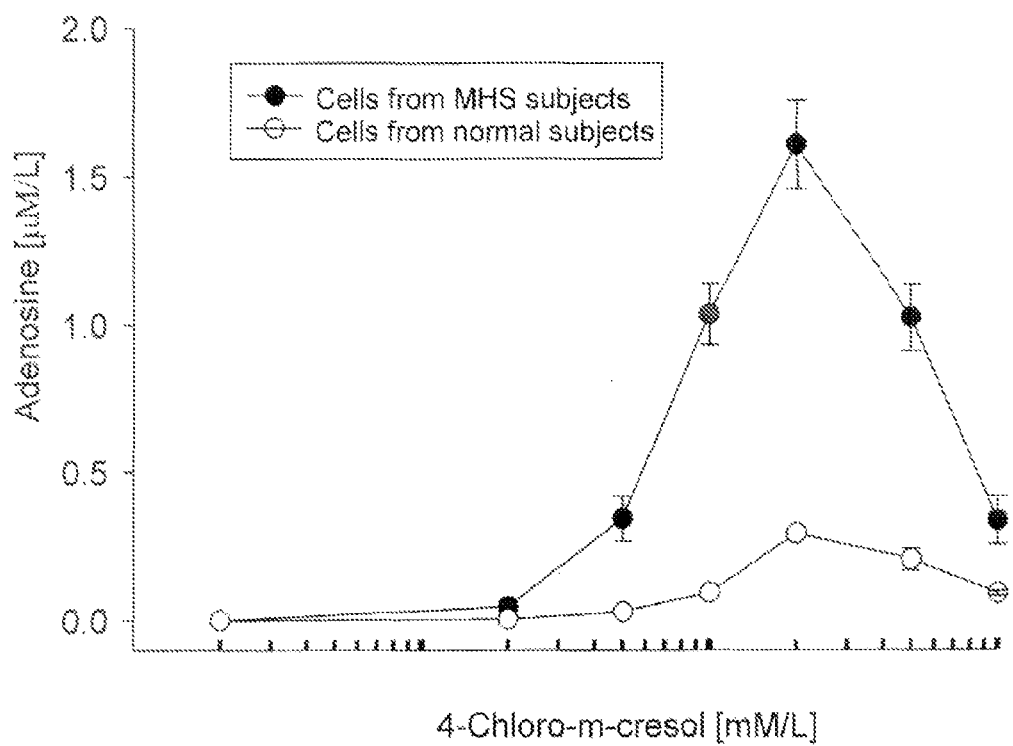
FIG. 5 shows a dose response curve for 4-chloro-m-cresol (4CmC)-induced intracellular adenosine in lymphocyte cells from malignant hyperthermia susceptible (MHS) and normal subject. Data were normalized per 1 million cells. Adenosine levels in MHS group were significantly higher than in the corresponding values in normal group.

As shown in FIG. 5, 4CmC stimulated inosine releases in a dose-dependent manner at concentrations above 1 mM reaching saturation at about 5 mM. Adenosine formation was not affected by 4CmC under the same conditions. The lack of adenosine responses to RyR1 stimulation was likely due to deamination of adenosine to inosine by the ubiquitous adenosine deaminase. To test this hypothesis, the lymphocytes were incubated with various concentrations of the adenosine deaminase blocker erthro-9(2-hydroxy-3nonyl)adenine (EHNA). As shown in FIG. 3, inosine formation decreased at EHNA concentrations of 10 μM or higher, and inosine formation decreased and was matched by an equimolar increase in adenosine, as expected. The data from FIGS. 2, 3 and combined showed that RyR1 stimulation by 4CmC caused a dose-dependent release of adenosine plus inosine in lymphocytes from MHS human subjects.

In the control human samples, i.e., in the absence of family or personal MH history as well as in cases where MHS was suspected but not diagnosed using the classical and independent caffeine halothane contracture test (negative CHCT, MHN group), the maximum effective dose of 4CmC (5 mM) did not, or minimally stimulated adenosine plus inosine formation. FIG. 2 compares the nucleoside responses from healthy controls as well as MHN subjects with those from MHS subjects. It is evident that the responses of MHS subjects were several-fold (about 4- to 6-fold) above the control responses measured in healthy controls and MHN subjects. In no case was there an overlap between the control MHN or normal control responses and the MHS responses. This is also demonstrated in FIG. 3 which indicates that 4CmC had only minor effects on nucleosides formation in normal and WIN samples compared to the almost 6-fold stimulation in MHS samples.

Specifically, baseline adenosine plus inosine levels were 2.7±0.5 (n=7), 1.7±0.5 (n=9), and 5.9±0.6 (n=11) µM in normal, MHN, and MHS groups, respectively. After 4CmC (5 mM) treatment, the nucleoside levels increased to 5.6±1, 5.4±0.6, and 35.6±3.1 µM in normal, MHN, and MHS groups, respectively. There were no overlaps between nucleoside levels in MHS group, MHN or normal groups. Data are presented as mean±SEM.

Thus, applicants have demonstrated that in human subjects RyR1 agonist stimulation can be used to test for RyR1-related diseases such as e.g., MHS. Accordingly, RyR1 agonist stimulation of lymphocyte cells and HPLC adenosine/inosine assay has potential for development of a minimally invasive, simple, and relatively economical method for diagnosing MHS in humans.

Example 2

In Vitro Studies for Detecting Malignant Hyperthermia Susceptibility in Swine

Figure 10:
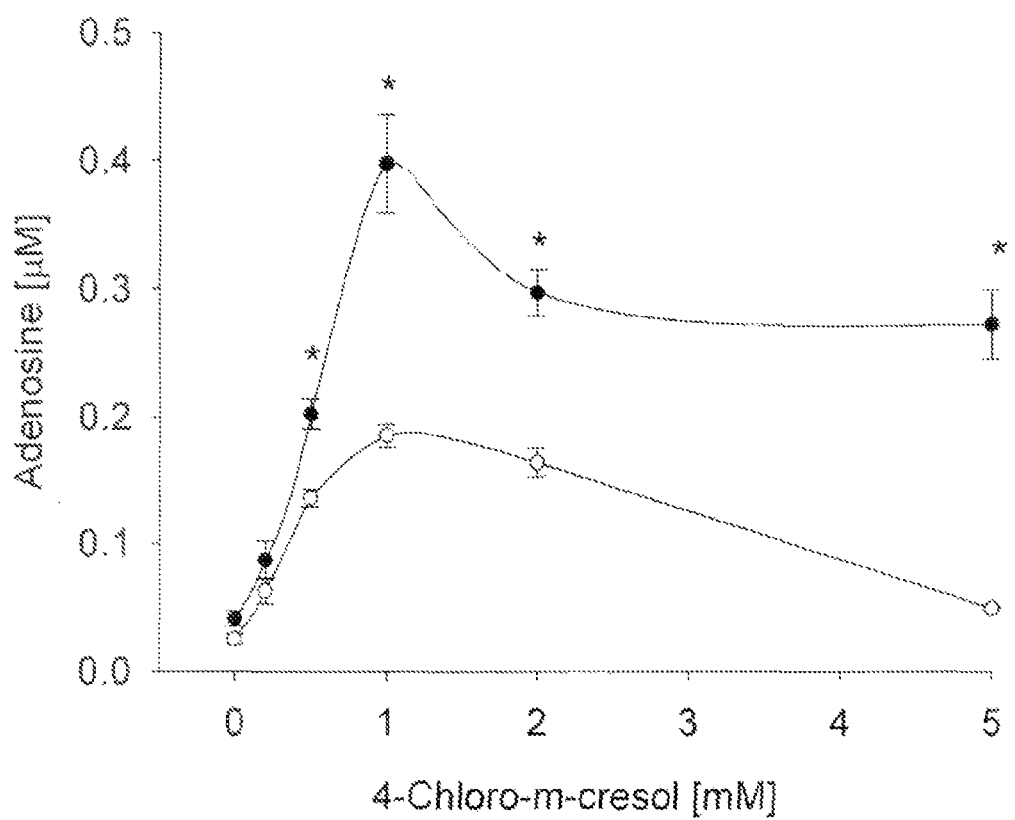
FIG. 10 shows the dose dependence of 4-chloro-m-cresol (4CmC)-induced adenosine in lymphocyte cells from normal swine (o) and swine carrying Arg615Cys mutation (•). Samples adenosine concentrations were normalized to reflect per 1 million cells. Cells (1 to 2 million) in suspension in normal Hanks' balanced salt solution in the presence of the adenosine deaminase inhibitor (EHNA, 0.1 mM) were incubated at 37° C. for 10 minutes. Following incubation, samples were treated with different 4CmC concentrations as indicated in the figure and were further incubated at 37° C. for additional 30 to 45 minutes. *4CmC responses at 0.5, 1, 2, and 5 mM on MHS group were significantly higher than the corresponding values in normal group with P values of 0.0035, 0.0035, 0.0017, and 0.0008 respectively.
Figure 11:
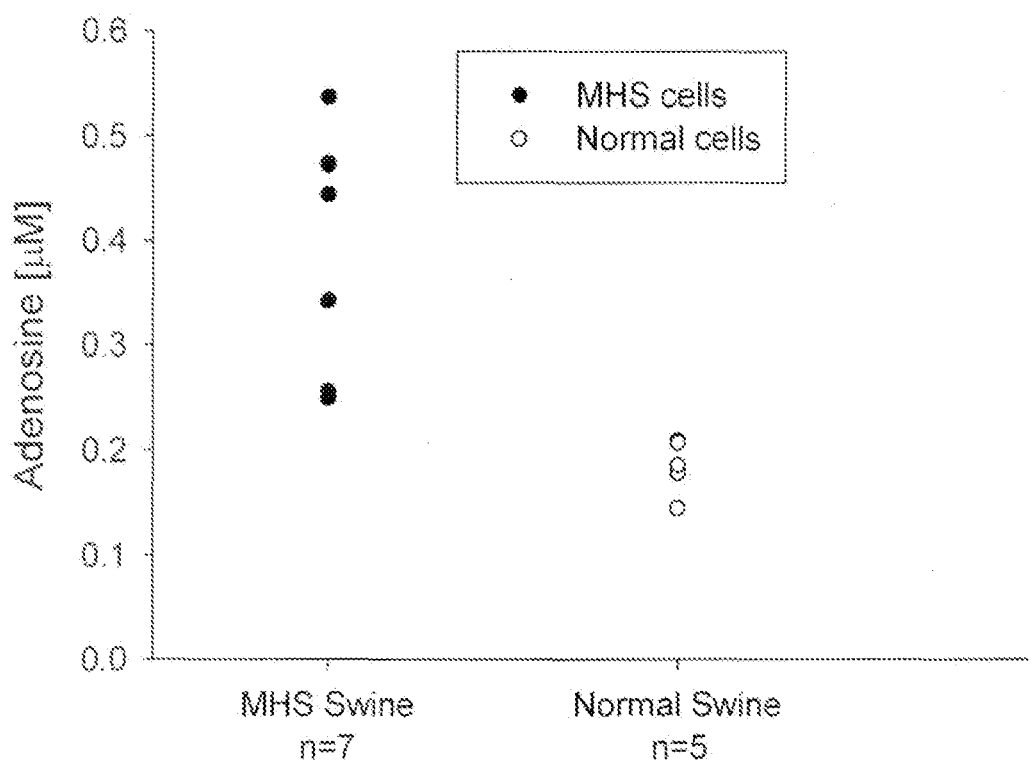
FIG. 11 shows the responses of 4-chloro-m-cresol (4CmC, 1 mM)-induced adenosine in lymphocyte cells from swine carrying Arg615Cys mutation (MHS, n=7) and normal swine (n=5). There were no significant differences between baselines adenosine levels in lymphocyte cells from MHS vs. normal swine.

Results similar to those of human studies were obtained in lymphocytes isolated from normal and MHS swine. The MHS pigs were homozygous with respect to their RyR1 mutation (in distinction to human MHS who were heterozygous with respect to their RyR1 mutation). Thus, swine lymphocytes stimulated with 5 mM 4CmC only increased adenosine plus inosine formation when MHS cells were tested. As shown in FIG. 11, 4CmC stimulation resulted in a nine-fold increase of nucleoside production in lymphocytes from the MHS group, while the same stimulation had minimal, if any, effect on nucleotide production in lymphocytes from normal swine (FIG. 10).

Lymphocyte cells were isolated from whole arterial blood sample (40 ml) obtained from homozygous recessive MHS (n=5) and normal (n=3) swine by the Ficoll-Hypaque centrifugation technique. Lymphocyte cells were then cultured in RPMI-1640 media supplemented with 10% fetal bovine serum plus 100 units/liter penicillin at 37° C. under 5% $CO_2$ for 2 to 3 weeks. After cell culture period, cell's ($5-15\times10^4$ cells) were suspended in Hanks' balanced salt solution (HBSS)+1% bovine serum albumin and treated with specific RyR1 agonist 4-chloro-m-cresol (4CmC, 5 mM) at 37° C. in the presence and absence of inhibitor of adenosine deaminase erythro-9-(2-hydroxy-3-nonyl) adenine (EHNA, 0.1 mM) for 30 minutes. After purification using 12% $HClO_4$ followed by centrifugation (10 minutes, 4000 RPM), aliquot of sample (50 µl) was assayed for adenosine and inosine content using high performance liquid chromatography (HPLC). Data are normalized to per 1 million cells, compared using one way ANOVA, and presented as mean±SEM. P<0.05 considered significant.

In this study un-immortalized lymphocyte cells were used and RyR1 agonist lymphocytes treatments were performed 2 to 3 weeks after blood drawn and isolation of lymphocyte cells as detailed in the method section. Further preliminary studies revealed that the RyR1 activator 4CmC produced significantly higher adenosine and/or inosine in lymphocyte cells 1 to 2 days after isolation in normal pigs. It appears that cell culture time period plays a role on nucleoside formation. These observations indicate that cell sensitivity to 4CmC correlates with the culture time periods.

Specifically, baseline adenosine plus inosine levels were 0.7±0.3 (n=3) and 0.8±0.3 (n=5) µM in normal and MHS groups, respectively. Upon stimulation of lymphocyte cells with 4CmC (5 mM) adenosine plus inosine levels increased to 1.16±0.3 and 8.06±0.9 µM in normal and MHS groups respectively. Again, there were no overlaps between adenosine plus inosine levels in MHS and normal swine.

Example 3

Adenosine Indexes RyR1 Agonist-Induced Calcium Overload in Lymphocytes from Malignant Hyperthermia (MH) Susceptible (MHS) Patients Definitive diagnosis for malignant hyperthermia (MH) susceptibility (MHS) is currently made by means of a caffeine halothane contracture test (CHCT). However, because of the invasive nature of the test, cost, and other associated risks, only about 10% of eligible patients undergo CHCT. Studies on human B cells have shown that the type 1 ryanodine receptor (RyR1) exists in B cells and that RyR1-mediated intracellular $Ca^{2+}$ release is higher in MHS than normal subjects.

After approval from the appropriate ethic committees for research involving humans, 30 individuals in following three groups were enrolled in the study: Group 1: MHS subjects with a positive CHCT (n=11); Group 2: MH suspicious patient but with negative CHCT results (MHN, n=11), and Group 3: normal subjects without MH family history or known neuromuscular disorder (n=8). Lymphocyte cells were isolated from whole venous blood sample (20 to 40 ml) by Ficoll-Hypaque centrifugation technique. Cells ($1-2\times10^6$) were suspended in Hanks' balanced salt solution (HBSS)+ 1% bovine serum albumin and then treated with HESS with different concentrations of specific RyR1 agonist 4-chloro-m-cresol (4CmC) at 37° C. in the presence of adenosine deaminase inhibitor erythro-9-(2-hydroxy-3-nonyl) adenine (EHNA, 0.1 mM) for 30 minutes. After purification steps, aliquots of sample (50 µl) were assayed for adenosine and inosine content using high performance liquid chromatography (HPLC). Data were normalized to per 1 million cells, analyzed using single factor ANOVA, and presented as mean±SEM. P<0.05 considered significant.

Figure 4:
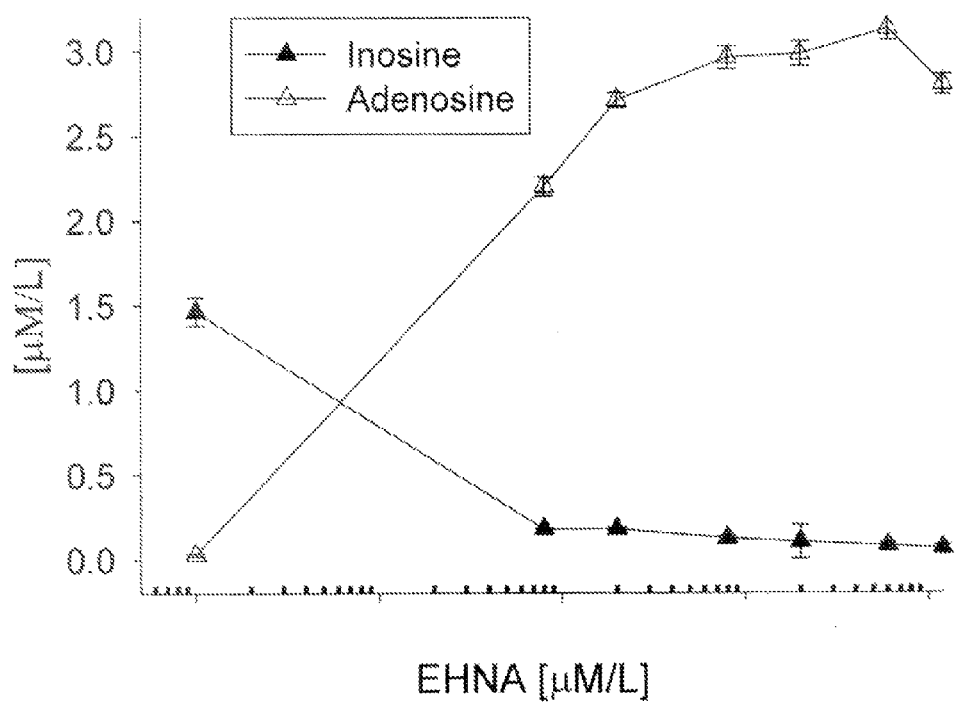
FIG. 4 shows an erythro-9(2-hydroxy-3-nonyl)adenine (EHNA) dose-response curve on 4-chloro-m-cresol (4CmC, 2 mM)-induced adenosine/inosine in immortalized B cells from a CHCT positive (MHS) subject. Adenosine and inosine values in the absence of EHNA are plotted against X=0.1 mM to allow logarithmic display of the entire dose response curves. Concentrations were normalized to per 1 million cells.
Figure 6:
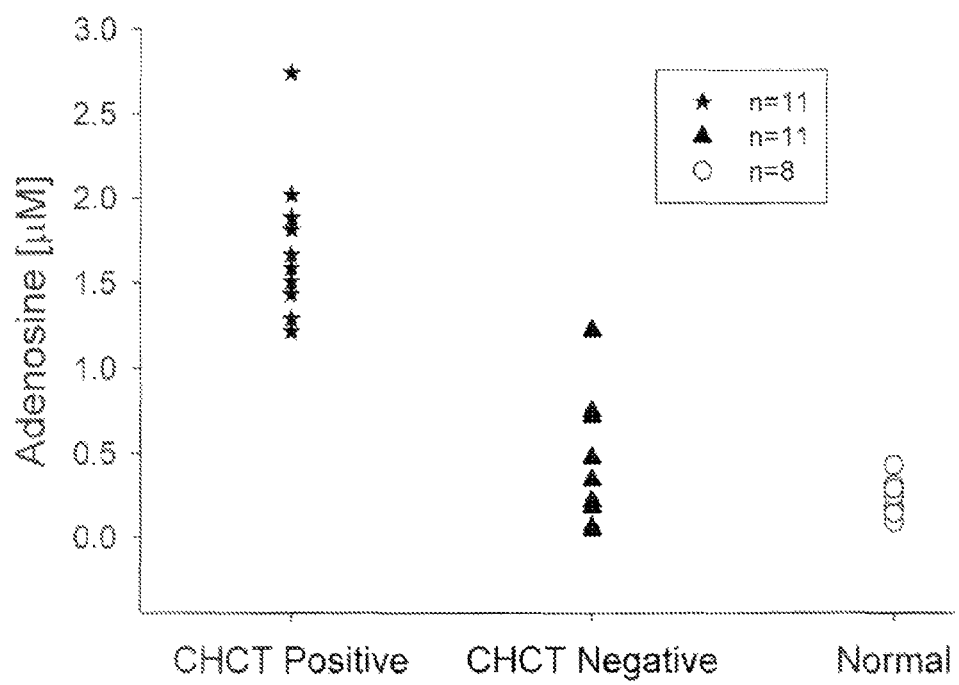
FIG. 6 shows the response of 4CmC (2 mM)-induced adenosine (ADO) in lymphocyte cells from CHCT positive, CHCT negative, and control subjects. 4CmC-induced increases in [ADO] in lymphocyte cells were significantly greater in CHCT-positive (MHS) than in CHCT-negative (MHN) or control groups (P<0.001). There were no significant differences in 4CmC-induced changes in ADO between the CHCT negative versus control group (P=0.39). Baseline ADO concentration was subtracted from its 4CmC-induced ADO concentration in each cell line.
Figure 7:
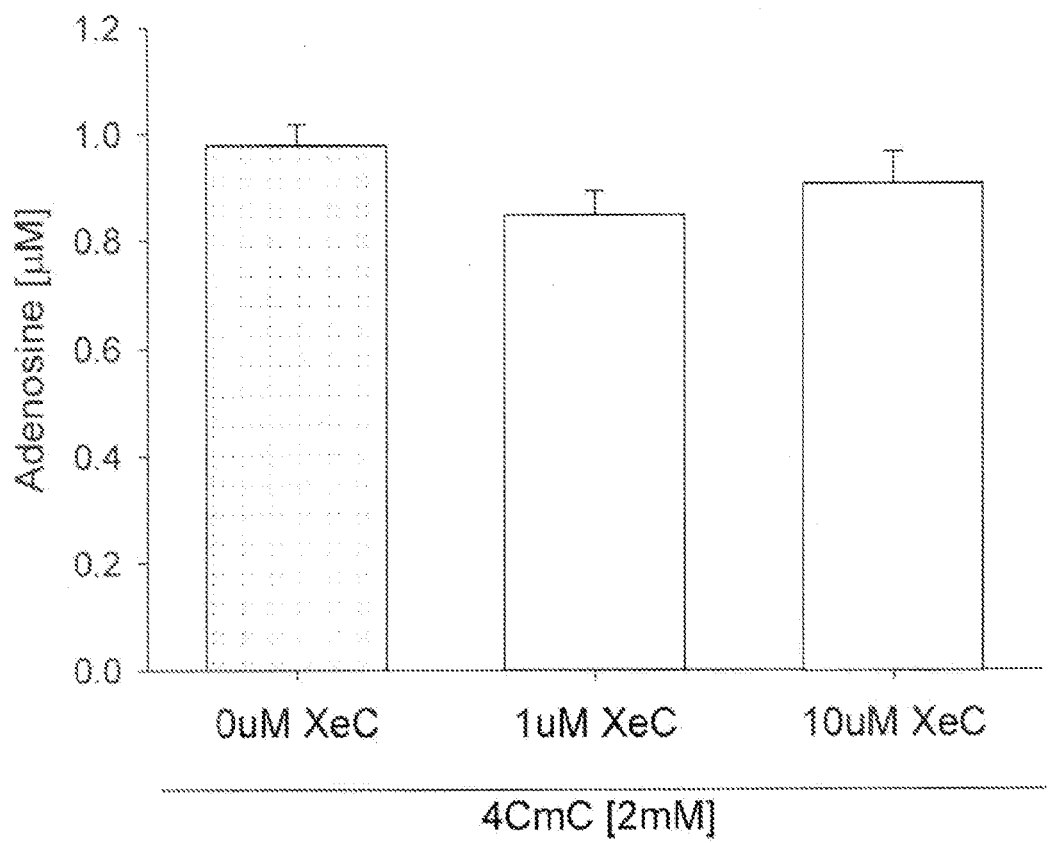
FIG. 7 shows the effect of Xestospongin C (XeC) on 4CmC induced adenosine. Briefly, immortalized B cells (MHS, n=3) in $Ca^{2+}$+ free HBSS buffer were treated with XeC (0, 1, and 10 mM) and incubated at 37° C. After a 10-minute incubation period, cells were treated with 2 mM 4CmC as described in Example 3.

As evident from FIG. 4, EHNA effectively inhibited ADO deaminase. In the presence of ADO deaminase inhibitor, ADO levels in control and MHS cells were 0.2±0.07 and 0.28±0.05 µM respectively. After 4CmC dose response treatment, ADO levels increased and maximized at 2 mM 4CmC to 0.61±0.11 and 1.71±0.13 µM in normal vs. MHS cells (P<0.001) (see FIG. 2). There were no overlaps in the ADO levels between 4CmC stimulated MHS cells and normal cells (see FIG. 6). Xestospongin C (XeC), a potent and selective inhibitor of the inositol triphosphate receptor (IP3R) was tested for 4CmC-induced ADO. XeC (1 and 10 µM) alone did not produce any change in the basal ADO levels (data not shown). XeC did not affect response of B Cells to 2 mM 4CmC (see FIG. 7).

The results depicted in FIGS. 4 to 7 demonstrate that:

i) RyR1-agonism-induced calcium release in B-cells produces energetic stress that is indexed by increased ADO formation;

ii) in MHS cells, 4CmC greatly increases the ADO formation, consistent with increased ATP catabolism due to loss of calcium control; and iii) the IP3 R appears not to play significant role in 4CmC-induced ADO.

Thus, the lymphocyte cells-adenosine system has clinical potential as a minimally invasive MH diagnostic test.

Example 4

4-Chloro-m-cresol Induces Adenosine in Lymphocyte Cells from Normal and Malignant Hyperthermia (MH) Mutation Carrying Swine: A MH Diagnostic Pilot Study A novel minimally invasive blood test for MH diagnosis (using lymphocyte cells isolated from swine carrying the MH mutation, Arg615Cys (MHS) and normal swine) was studied. The experiments were designed to a) examine the hypothesis that mutations in the RyR1 gene that lead to abnormal agonist-induced $Ca^{2+}$ release in skeletal muscle will also lead to irregular ADO release in lymphocyte cells and weather the lymphocyte cell assay can be used as a diagnostic tool for MH and b) to determine whether ADO release is correlated with major intracellular $Ca^{2+}$ pools such as $IP_3$, mitochondria, and RyR1.

4-Chloro-m-cresol (4CmC) was used to stimulate lymphocyte cells. 4CMC mimics the effects of caffeine and halothane to selectively induce release of intracellular $Ca^{2+}$ in several skeletal muscle preparations (see Baur et al., *Anesth Analg* 90:200-5 (2000)) as well as in isolated SR vesicles (see Choisy et al., *J Pharmacal Exp Ther* 290:578-86 (1999)).

Animal model: With approval of the Uniformed Services University of the Health Sciences' institutional animal care and use committee, seven (7) normal pigs (not MH sensitive, Archer Farm, Darlington, Md.) and seven (7) homozygous MHS swine (Boyle Farms, Moorehead, Iowa) were sedated with ketamine (8-10 mg/kg, 1M), an ear vein cannulated and anesthesia induced with propofol (0.2-0.4 mg/kg/min) while mechanically ventilated. The MHS swine were carrying an Arg615Cys mutation (MHS) and confirmed to be CHCT positive. Effort was made to match the two experimental animal groups in regard to factors such as gender, age, or weight. A 20 GA cannula was inserted percutaneously into the superficial femoral artery. Blood pressure, heart rate, respiratory rate, $ETCO_2$, and body temperature were monitored continuously. After physiological parameters were stabilized arterial blood samples (40 ml) were withdrawn in heparinized 60 ml syringe. After collection of blood samples, skeletal muscle biopsy (Vastus lateralis) for CHCT was performed accordingly to a previously described protocol (see Larach M G. *Anesth Analg* 69:511-5 (1989)).

Isolation of lymphocytes from whole blood: Lymphocyte cells were isolated from whole blood by Ficoll-Hypaque density gradient centrifugation technique (see Boyum A., *Scand. J. Clip. Lab.* 97:77-89 (1968)). Isolated lymphocyte cells were dispensed into 3-volume normal Hanks' balanced salt solution (HBSS) and centrifuged (10 minutes at 1000 RPM). The pellet was re-suspended in HBSS to lyse contaminating erythrocytes and spun. The later step was repeated one more time. To maintain simplicity of the protocol for possible MH diagnostic purposes no further purification was attempted. Lymphocyte cells were then cultured in RPMI-1640 media supplemented with 10% fetal bovine serum, 100 units/liter penicillin and 2 mM glutamine. Cell cultures were incubated at 37° C. in a humidified chamber with 5% $CO_2$. All experiments were completed within 4 days after isolation of lymphocyte cells from whole blood samples.

Nucleosides Assay Protocol: Briefly, lymphocyte cells ($1-2\times10^6$ cells/test) were suspended in HBSS with or without $Ca^{2+}/Mg^{2+}$ (as indicated for each experiment) plus 0.1% bovine serum albumin (BSA). Experiments were carried out in the presence of the adenosine deaminase inhibitor erythro-9-(2-hydroxy-3-nonyl) adenine-HCl (EHNA, 0.1 mM) to prevent deamination of adenosine to inosine (Lorbar et al., *J Mol Cell Cardiol* 31: 401-12 (1999)) and incubated at 37° C. for 10 minutes followed by treatment with different 4CmC concentrations (0.05-10 mM). Further incubation at 37° C. for an additional 45 minutes was also carried out. Final volumes of the test tubes were adjusted to 0.2 ml using HBSS buffer. Termination of the cell activity and purification of samples was accomplished by addition of 0.1 ml 12% perchloric acid followed by centrifugation at 5000 RPM for 10 minutes. Aliquots of the supernatant (50 µl) were assayed for adenosine and inosine content using HPLC.

HPLC Conditions: The HPLC system consisted of a Waters Symmetry $C_{18}$ column (4.6×250 mm) and mobile phase of 94% $KH_2PO_4$ (50 mM, pH 4.6) containing 1-heptanesulfonic acid (0.5 mM) and 6% acetonitrile. Under these conditions, retention times for inosine and adenosine were 4 and 7.3 min, respectively. Peak width of inosine and adenosine were 18 and 36 seconds, respectively. Eluting compounds were detected by their absorbance at 254 nm using a Waters photodiode array detector (model 996). Sample adenosine and inosine concentrations were obtained using a calibrated standard curve of concentrations vs. peak area.

Statistics: Sample nucleosides concentrations were normalized to represent per 1 million cells and presented as means±SEM. The t-test was applied to test for differences between agonist-induced nucleosides in lymphocyte cells from MHS and normal swine. A P<0.05 considered to indicate statistical significance.

Reagents: HBSS containing $Ca^{2+}/Mg^{2+}$ (referred to as normal HBSS) and $Ca^{2+}/Mg^{2+}$ free HBSS were from Invitrogen/GIBCO, Carlsbad, Calif., USA. Adenosine deaminase inhibitor, erythro-9(2-hydroxy-3-nonyl) adenine (EHNA, Sigma-Aldrich) was dissolved either in normal HBSS or $Ca^{2+}/Mg^{2+}$ free HBSS (Sigma-Aldrich, USA) and stored at −20° C. $KH_2PO_4$, 1-heptanesulfonic acid, bovine serum albumin, ADO, inosine, and other ordinary laboratory chemicals were from Sigma-Aldrich, USA. RPMI-1640 culture media, fetal bovine serum, and penicillin were from Quality Biological, Inc., USA. 4-Chloro-m-cresol (Sigma-Aldrich, USA) was prepared daily in distilled water. Carbonyl cyanide 4-(trifluoromethoxy) phenylhydrozone (FCCP, Sigma-Aldrich) and Xestospongin C (XeC, Calbiochem, USA) were dissolved in dimethyl sulfoxide (DMSO, Sigma-Aldrich, USA) and stored at −20° C. Azumolene (gift from Dr. Jerry Parness, Department of Anesthesiology, University of Pennsylvania) was dissolved in DMSO and stored at −20° C.

Results

Although seven (7) lymphocyte cell lines in each group of MHS and normal swine were examined the number of cell lines in each protocol was variable due to limited availability of cells.

Figure 8:
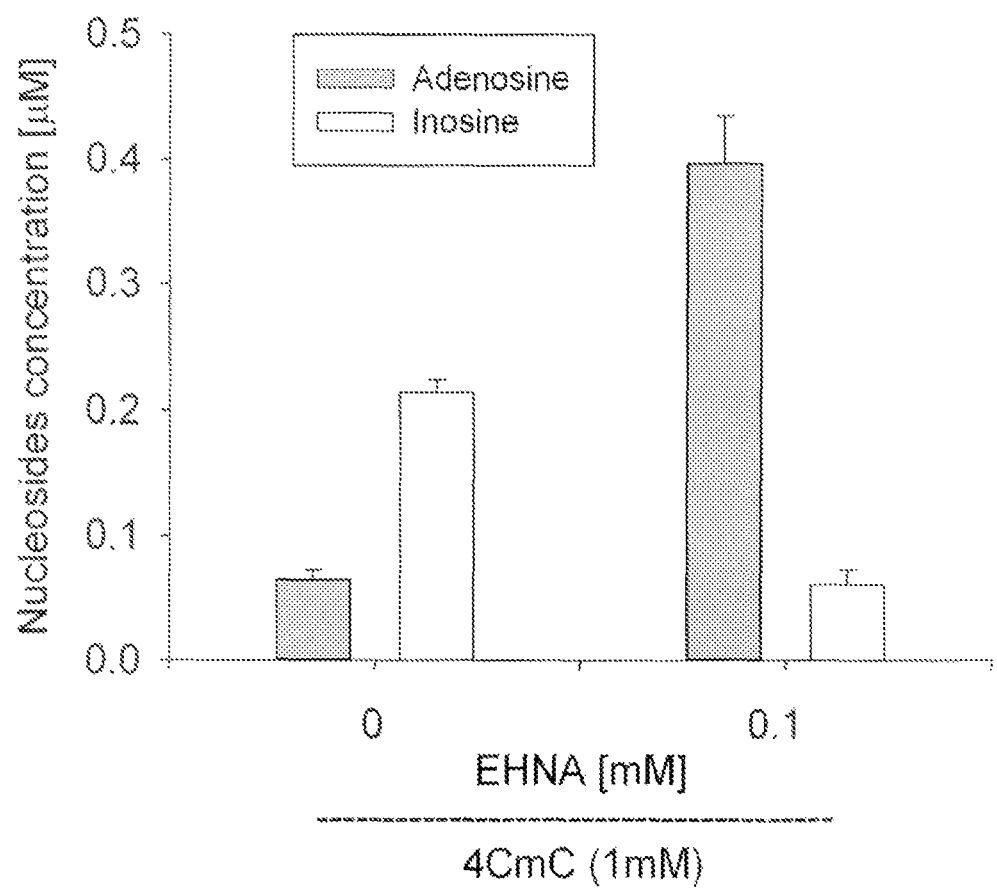
FIG. 8 shows the effect of 1 mM 4-chloro-m-cresol (4CmC)-induced adenosine/inosine in lymphocyte cells from swine carrying Arg615Cys mutation and having positive caffeine halothane contracture test (MS) in the presence and absence of adenosine deaminase inhibitor erythro-9(2-hydroxy-3-nonyl) adenine (EHNA, 0.1 mM). Sample nucleoside concentrations were normalized to reflect per million cells. Lymphocyte cells (1 to 2 million) from MHS swine (n=4) treated with HBSS with and without EHNA bathed at 37° C. for 10 minutes. Following a 10-minute incubation period, samples were treated with 4CmC to achieve final concentration of 1 mM as indicated in the figure.

FIG. 8 shows 4CmC (1 mM)-induced ADO/inosine in the presence and absence of 0.1 mM EHNA. The lack of adenosine responses to 4CmC stimulation was due to deamination, of adenosine to inosine by the ubiquitous adenosine deaminase. To examine this, lymphocyte cells were incubated with various concentrations of the adenosine deaminase blocker EHNA. The results demonstrated that at EHNA concentrations of 20 µM or higher inosine formation decreased and ADO concentration increased to plateau level (n=3, EHNA dose-response data not shown). The differences in the molar concentrations of inosine and ADO in FIG. 8 were likely due to metabolism of inosine to hypoxanthine by purine nucleoside phosphorylase and, at least in part, also due to the differences in the molar absorption coefficient (c) of inosine compared with ADO; at the measuring wavelength of $\lambda=254$ nm for detection of the nucleosides (ADO: $\lambda_{max}=258$ nm, $\epsilon=15,100$; Inosine: $\lambda_{max}=248$ nm, and $\epsilon=12,200$ (see Merck Index)) ADO absorbance is nearly 24% higher than that of inosine.

Figure 9:
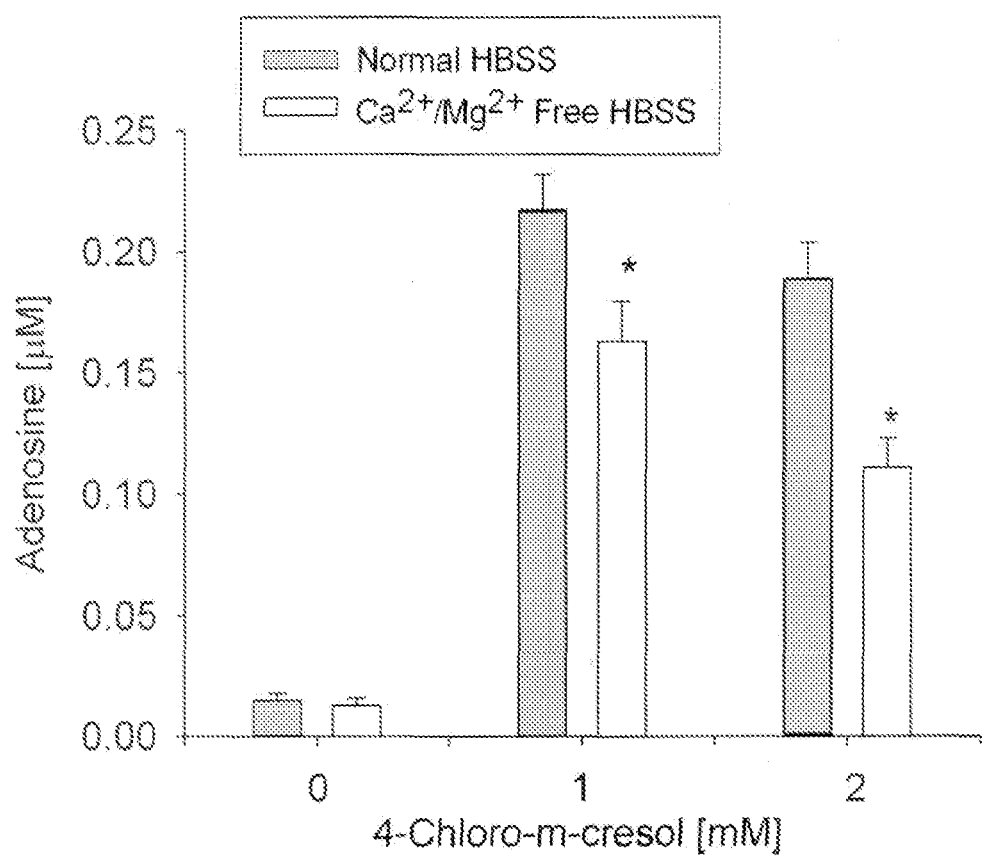
FIG. 9 shows the effect of external $Ca^{2+}/Mg^{2+}$ on 4-chloro-m-cresol (4CmC)-induced adenosine. Lymphocyte cells (1 to 2 million) from normal swine (n=6) bathed for 10 minutes in Hanks' balanced salt solution (HBSS) with and without $Ca^{2+}/Mg^{2+}$ and containing adenosine deaminase inhibitor (EHNA, 0.1 mM). Following a 10-minute incubation period, samples were treated with 4CmC (1 and 2 mM) as indicated in the figure. * 4CmC induced adenosine levels in the absence of external $Ca^{2+}/Mg^{2+}$ were significantly lower compared with corresponding values when experiment was performed in the present of external $Ca^{2+}/Mg^{2+}$.

Effect of External $Ca^{2+}/Mg^{2+}$ on 4CmC-Induced ADO Formation:

There were no differences between the basal resting ADO levels of lymphocyte cells from normal swine (n=6) incubated in normal $Ca^{2+}$-containing HBSS and $Ca^{2+}/Mg^{2+}$-free HBSS: $0.023\pm0.005$ and $0.02\pm0.004$ µM, P>0.05, respectively. However, using 1 mM 4CmC to induce ADO in normal HBSS vs. $Ca^{2+}/Mg^{2+}$-free HBSS, the following was measured $0.326\pm0.023$ vs. $0.244\pm0.026$ µM, P=0.037, respectively; this reflected a 25.2±5.1% increase in ADO formation in the presence of normal levels of extracellular $Ca^{2+}$. At 2 mM 4CmC, the difference increased to $0.284\pm0.023$ in presence and $0.167\pm0.018$ µM in the absence of extracellular $Ca^{2+}$ reflecting a 41±3.3% increase in 4CmC-induced ADO formation (P=0.002, FIG. 9) in the presence of extracellular $Ca^{2+}$. The data suggested that removal of external $Ca^{2+}/Mg^{2+}$ eliminated $Ca^{2+}/Mg^{2+}$ influx across the plasma membrane in presence of 4CmC and that this transmemebrane $Ca^{2+}$ influx contributed to the overall $Ca^{2+}$ dysregulation during stimulation by 4CmC to release $Ca^{2+}$ from the sarcoplasmic reticulum. The ADO formation observed in $Ca^{2+}$-free HBSS likely reflected the energetic stress and ATP catabolism due to $Ca^{2+}$ release exclusively from intracellular stores, the SR in particular. This effect of extracellular $Ca^{2+}$ on 4CmC-induced ADO formation accounted for 59% to 76% of total ADO production under these conditions.

4CmC-Induced ADO:

Experiments for 4CmC dose-response relations were carried out in normal $Ca^{2+}$ containing HBSS. Shown in FIG. 10 are 4CmC dose-response data for lymphocyte cells from normal (n=7) and MHS (n=7) swine. Lymphocyte ADO levels increased upon 4CmC stimulation dose-dependently and peaked at near 1 mM 4CmC, reaching $0.389\pm0.033$ and $0.199\pm0.005$ µM in MHS vs. normal cells (P=0.0035), respectively. The estimated $EC_{50}$ values for MHS and normal cells were $0.55\pm0.06$ and $0.34\pm0.04$ mM 4CmC, respectively, demonstrating an almost 60% increase in sensitivity in the MHS cell population. FIG. 11 shows that the individual ADO levels due to 4CmC (1 mM) from MHS cells did not overlap with those from normal cells. Subtraction of the baseline ADO values confirmed this result. The basal plus 4CmC (1 mM)-induced ADO ranges for normal and MHS cells were 0.145-0.209 and 0.250-0.537 µM, respectively.

Figure 12:
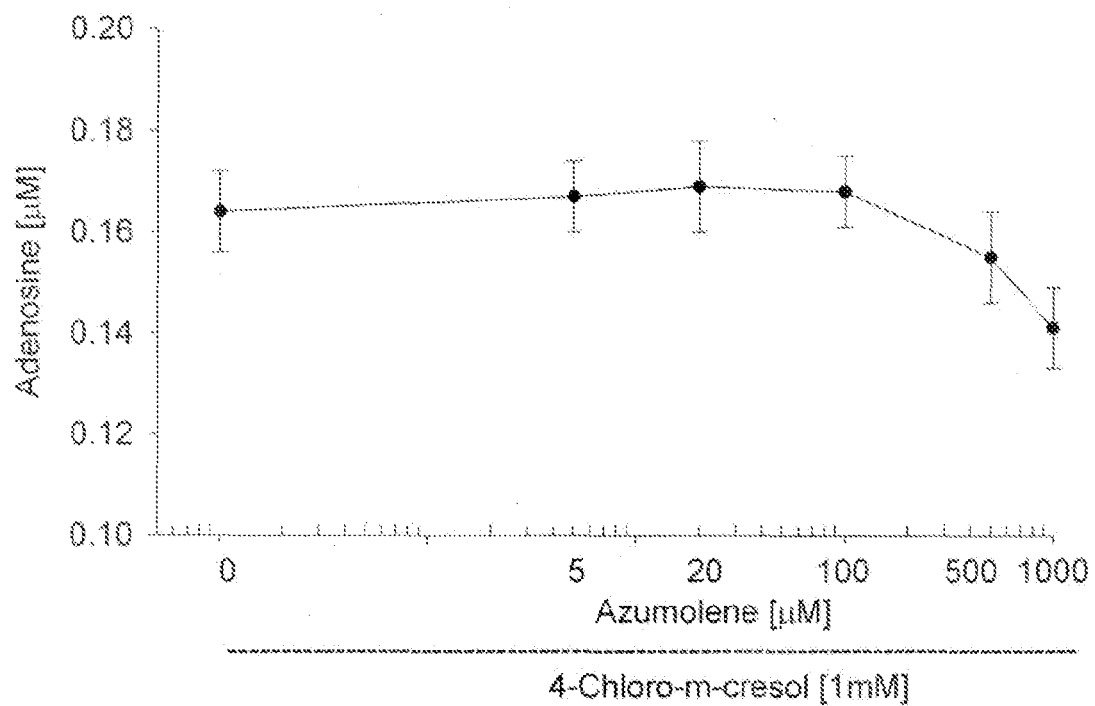
FIG. 12 shows the effect of azumolene (0-1000 mM) on 4-chloro-m-cresol (4CmC, 1 mM))-induced adenosine. Lymphocyte cells (1 to 2 million) from normal swine (n=5) in suspension in $Ca^{2+}/Mg^{2+}$-free Hanks' balanced salt solution and in the presence of adenosine deaminase inhibitor, with and without azumolene were incubated at 37° C. for 10 minutes. At the end of the incubation period, samples were treated with 1 mM 4CmC and bathed for an additional 30 to 45 minutes. Measured adenosine level in the absence of azumolene (4CmC induced-adenosine in the absence of azumolene) was plotted against X=0.1 mM to allow logarithmic display of the entire dose-response curve. Azumolene in the concentrations range used did not significantly affect 4CmC-induced adenosine.

Effect of Azumolene:

The effect of the membrane-permeable RyR inhibitor azumolene was examined in 4CmC-treated cells. According to the literature, azumolene is a more potent and more soluble RyR antagonist than the clinically used RyR inhibitor dantrolene (see el-Hayek et al., Biochem Biophys Res Commun 187:894-900 (1992)). Lymphocyte cells in the presence of EHNA were treated with DMSO (final DMSO concentration 10% V/V) with and without different concentrations of azumolene (0-1000 µM), incubated at 37° C. for 10 minutes and subsequently treated with 1 mM 4CmC. As shown in FIG. 12, azumolene in concentrations up to 1 mM only marginally inhibited 4CmC-induced ADO formation. (Non-linear curve fitting of these data suggested an apparent Ki value near 5 mM azumolene (unpublished observations)). In an attempt to increase permeability of azumolene across the plasma membrane, 30% (V/V) DMSO (n=3) was tested as a carrier vehicle. Results suggested that 30% DMSO concentration is toxic to the cells, causing significant decrease in the 4CmC-induced ADO (data not shown).

Figure 13:
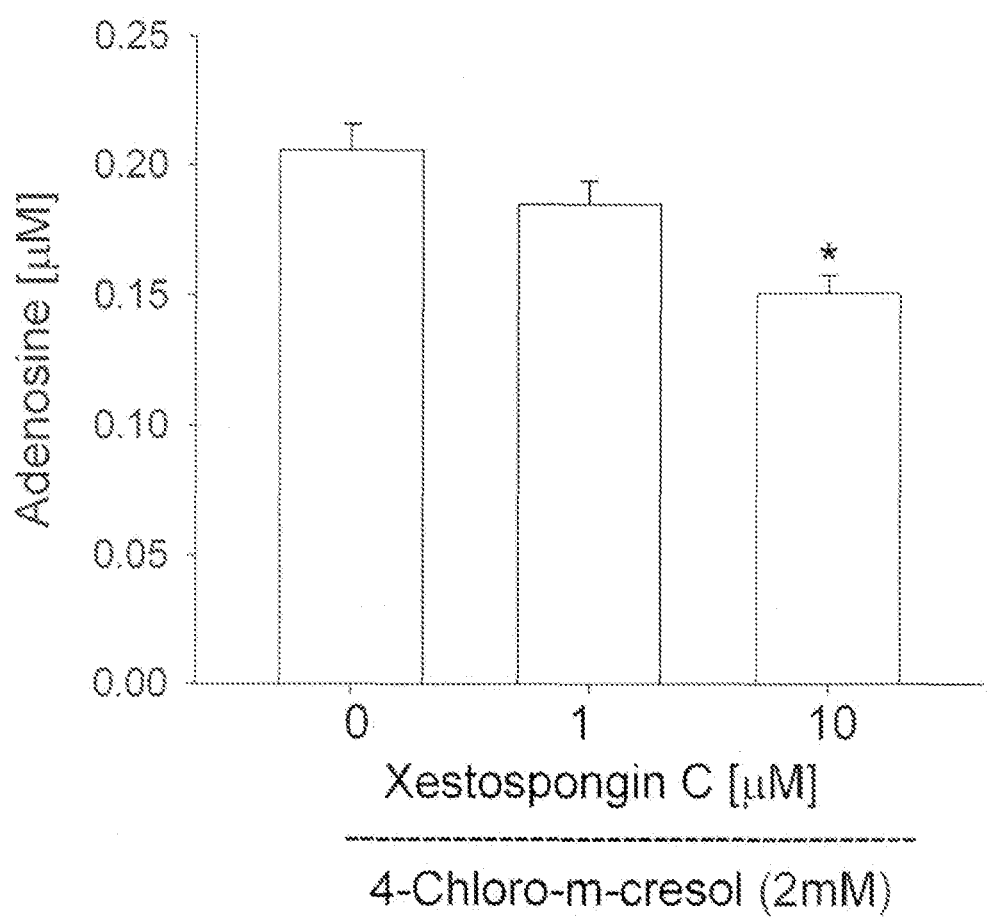
FIG. 13 shows the effect of Xestospongin C (XeC) on 4-chloro-m-cresol (4CmC)-induced adenosine. Lymphocyte cells (1 to 2 million) from normal swine (n=5) bathed in $Ca^{2+}/Mg^{2+}$ free Hanks' balanced salt solution in the presence of adenosine deaminase inhibitor. Samples were treated with XeC as indicated in the figure and incubated for 10 minutes at 37° C. At the end of the incubation period samples were treated with 2 mM 4CmC.

Effect of Xestospongin C (XeC):

XeC is a potent and selective inhibitor of the inositol trisphosphate receptor ($IP_3R$) coupled to a special intracellular pool of $Ca^{2+}$ (Miyamoto et al., Br. J. Pharmacol 130: 650-4 (2000); Ibarra et al., Biol Chem 279: 7554-65 (2004); De Smet et al. Cell Calcium 26:9-13 (1999)). To determine if $IP_3R$ contributed to the observed 4CmC-induced ADO formation, lymphocyte cells in suspension in $Ca^{2+}/Mg^{2+}$-free HBSS were treated with DMSO (10% V/V final concentration) with and without XeC (1 and 10 µM). FIG. 13 summarizes the observed effects of XeC on 4CmC-induced ADO. XeC (1 and 10 µM) alone did not affect the basal ADO levels (data not shown). Similarly, 1 µM XeC did also not affect 4CmC-induced ADO. However, 10 µM XeC significantly decreased 4CmC-induced ADO by 27%, suggesting that $IP_3R$-coupled intracellular $Ca^{2+}$ stores in porcine lymphocyte cells may contribute, at least in part, to $Ca^{2+}$ dysregulation caused by 4CmC, which in turn is reflected indirectly in the observed ADO formation (see FIG. 10).

Effect of FCCP on 4CmC-Induced ADO in Lymphocyte Cells:

Mitochondria are the site of oxidative phosphorylation and may also serve as a source of intracellular $Ca^{2+}$; these organelles have been shown to express RyRs on the outer mitochondrial membrane. FCCP is an uncoupler of oxidative phosphorylation causing depolarization of the inner mitochondrial membrane, which in turn leads to depletion of the mitochondrial matrix $Ca^{2+}$ (Beutner et al. J Biol Chem 276: 21482-8 (2001)). FCCP (2 and 20 µM) alone significantly increased basal ADO levels (4.5 fold) to around 0.1-0.12 µM (FIG. 14A), but this effect was small compared to the 4CmC effect. FCCP was only 25% as effective in induced ADO formation as 4CmC (see FIG. 10). Interestingly, both tested FCCP concentrations prevented the maximum increase in ADO formation when 1 mM 4CmC was used during FCCP treatment (see FIG. 14 B). Without being bound by theory, this data suggests that mitochondrial $Ca^{2+}$ irregularities could be contributing to the 4CmC-induced ADO release in swine lymphocyte cells (see FIG. 14 B). It is however unclear whether such mechanism would require that 1 mM 4CmC depolarizes the mitochondrial membrane or that binding of 4CmC to the putative mitochondrial RyRs is prevented during mitochondrial depolarization. Because of limited availability of porcine MHS lymphocyte cells, FCCP effects on MHS cells and its interaction with the RyR1 agonist 4CmC were not assessed.

CHCT Results: Halothane (3%)-induced contractures in muscle strips from MHS and normal swine were 19.2±3.1 mN (range: 11.2-33.1 mN) and 1.2±1.0 mN (range: 0-1.8 mN), respectively. Caffeine (2 mM)-induced contractures in muscle strips from MHS and normal swine were 10.2±1.8 mM (range: 4.7-17.1 mN) and 0.4mN (range: 0-1 mN), respectively.

The experimental results can be summarized as follows: 4CmC treatment of lymphocyte cells from MHS and normal swine produces energetic stress that is indexed by increased ADO formation. 4CmC-induced ADO release in lymphocyte cells from MHS swine was significantly greater than in cells from normal swine, consistent with increased adenosine-5'-triphosphate (ATP) catabolism due to loss of calcium control. There was no overlap between 4CmC-induced ADO in lymphocyte cells from MHS swine compared with those of normal cells. Extracellular $Ca^{2+}$ contributes significantly to 4CmC-induced ADO release in swine lymphocyte cells that is likely due to influence of $Ca^{2+}$ influx. Azumolene, a potent RyR1 inhibitor, in the concentrations range used did not significantly decrease 4CmC-induced ADO in lymphocyte cells from normal swine. Both $IP_3R$ and mitochondria appears to play a role in 4CmC-induced ADO. Although the numbers of the lymphocyte cells studied were relatively low the data clearly distinguished between normal and swine carrying the Arg614Cys mutation in their RyR1 receptors, which is causative for the MH disease in swine.

The experiments illustrated in the Examples demonstrate substantially increased nucleoside production during stimulation with calcium channel agonists, e.g., RyR1 agonists, in both human and porcine lymphocytes. This discovery provides the basis for a novel, minimally invasive, relatively simple, relatively inexpensive diagnostic test for MH susceptibility, which additionally is free from local side-effects of current diagnostics employing the invasive CHCT or IVCT paradigms. The new technique also has potential for diagnosing other skeletal muscle-related disorders, including rhabdomyolysis, as outlined above in the introduction section. This discovery provides the basis for a novel, minimally invasive, relatively simple, relatively inexpensive diagnostic test for calcium channel related diseases.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. Furthermore, the embodiments are intended to cover the components and steps in any sequence which is effective to meet the objectives their intended, unless the context specifically indicates the contrary. All references, patents, and patent applications referred to in this application are herein incorporated by reference in their entirety.

What is claimed is:

1. A method for detecting an RyR1 related disease selected from the group consisting of malignant hyperthermia, central core disease, multiminicore disease and nemaline rod myopathy in a subject comprising:
   (a) contacting lymphocytes isolated from the subject with an RyR1 agonist selected from the group consisting of 4-chloro-m-cresol, ryanodine, halothane, thiopental, caffeine or mixtures thereof;
   (b) measuring the adenosine and inosine in culture medium produced by the lymphocytes in culture; and
   (c) comparing the measured levels in the sample to the adenosine and inosine levels in a normal control, wherein an increase in the adenosine and inosine levels relative to the control is indicative of an RyR1 related disease.

2. The method of claim 1, wherein the RyR1-related disease is malignant hyperthermia.

3. The method of claim 1, wherein the RyR1 agonist is 4-chloro-m-cresol.

4. The method of claim 1, wherein the lymphocytes are in a blood sample from the subject.

5. The method of claim 1, wherein the lymphocytes are peripheral blood lymphocytes.

6. The method of claim 1, wherein the normal control comprises levels of adenosine and inosine produced by lymphocytes from a subject not suffering from an RyR1-related disease.

7. The method of claim 1, wherein an increase in the adenosine and inosine levels relative to the control is indicative of a deletion or mutation in a gene controlling the expression and/or function of RyR1.

8. The method of claim 7, wherein the deletion or mutation in the RyR1 gene is indicative of a skeletal muscle-related disorder.

9. The method of claim 1, wherein said subject is a human.

10. The method of claim 1, wherein said subject is a pig.

11. The method of claim 1, wherein the method comprises from about 0.1 mM to about 10 mM of an RyR1 agonist.

* * * * *